United States Patent [19]

Stetter et al.

[11] 4,337,268
[45] Jun. 29, 1982

[54] COMBATING FUNGI WITH N-OXIMINOALKYL-ANILIDES

[75] Inventors: Jörg Stetter, Wuppertal; Wilhelm Brandes, Leichlingen, both of Fed. Rep. of Germany

[73] Assignee: Bayer Aktiengesellschaft, Leverkusen, Fed. Rep. of Germany

[21] Appl. No.: 150,261

[22] Filed: May 15, 1980

[30] Foreign Application Priority Data

Jun. 5, 1979 [DE] Fed. Rep. of Germany ....... 2922759

[51] Int. Cl.³ .................... A01N 37/22; C07C 307/68; C07D 103/175
[52] U.S. Cl. ................................. 424/285; 424/272; 424/273 P; 424/273 R; 424/275; 424/283; 424/302; 424/303; 424/304; 424/309; 424/324; 542/416; 548/248; 548/262; 548/341; 548/378; 260/454; 260/455 A; 260/456 A; 260/465 D; 564/123; 564/189; 564/190; 564/192; 564/202; 564/212; 549/72; 549/487; 549/419
[58] Field of Search ................... 560/9, 24, 27, 29, 33, 560/190, 197; 564/123, 189, 190, 202, 192, 212; 260/345.7, 456 A, 454, 465 D, 347.2, 455 A, 347.3; 424/302, 303, 304, 309, 324, 272, 273 R, 273 P, 275, 283, 285; 548/248, 378, 341, 262; 549/72; 542/416; 546/192

[56] References Cited

U.S. PATENT DOCUMENTS 3,852,332 12/1974 Cross et al. .................... 560/29
4,093,738 6/1978 Hubele .......................... 260/454
4,174,210 11/1979 Schinski et al. ................ 260/347.3

FOREIGN PATENT DOCUMENTS 2019404 of 0000 United Kingdom .

OTHER PUBLICATIONS

Hubele, Chem. Abstracts, vol. 90, (1979) 54799u.
JCS Chemical Communication, 1978, p. 124.

Primary Examiner—Henry R. Jiles
Assistant Examiner—Bernard Dentz

Attorney, Agent, or Firm—Sprung, Horn, Kramer & Woods

[57] ABSTRACT

N-Oximinoalkyl-anilides of the formula

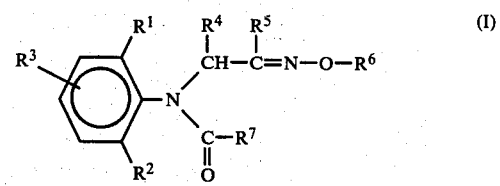

in which
  $R^1$ represents hydrogen, alkyl or halogen,
  $R^2$ represents hydrogen or alkyl,
  $R^3$ represents hydrogen or alkyl,
  $R^4$ represents hydrogen or alkyl,
  $R^5$ represents hydrogen or alkyl,
  $R^6$ represents hydrogen, alkyl, alkenyl, alkynyl, alkoxyalkyl, alkylthioalkyl or optionally substituted aralkyl and
  $R^7$ represents furyl, tetrahydrofuryl, thiophenyl, or tetrahydrothiophenyl; isoxazolyl which is optionally substituted in alkyl; alkyl, alkenyl or alkynyl, in each case optionally substituted by cyano or thiocyano; dihalogenoalkyl or cycloalkyl; or the grouping $-CH_2Az$, $-CH_2-OR^8$, $-CH_2-SR^8$, $-OR^8$, $-SR^8$, $-CH_2-OSO_2R^8$, $-COOR^8$ or

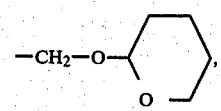

wherein
  $R^8$ represents an optionally substituted alkyl, alkenyl, alkynyl or alkoxyalkyl radical and
  Az represents pyrazol-1-yl, 1,2,4-thiazol-1-yl or imidazol-1-yl, which possess fungicidal activity.

10 Claims, No Drawings

COMBATING FUNGI WITH N-OXIMINOALKYL-ANILIDES

The present invention relates to certain new N-oximinoalkyl-anilides, to a process for their preparation and to their use as fungicides.

It has already been disclosed that certain halogenoacetanilides, for example N-chloroacetyl-N-(2-ethyl-6-methylphenyl)-alanine methyl ester, can be employed with good success for combating fungal plant diseases (see DE-OS (German Published Specification) 2,350,944). However, their action is not always completely satisfactory, especially when small amounts and low concentrations are used, and in particular when combating Phytophthora species.

The present invention now provides, as new compounds, the N-oximinoalkyl-anilides of the general formula

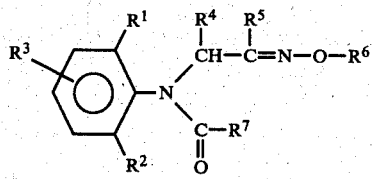
(I)

in which
R$^1$ represents hydrogen, alkyl or halogen,
R$^2$ represents hydrogen or alkyl,
R$^3$ represents hydrogen or alkyl,
R$^4$ represents hydrogen or alkyl,
R$^5$ represents hydrogen or alkyl,
R$^6$ represents hydrogen, alkyl, alkenyl, alkynyl, alkoxyalkyl, alkylthioalkyl or optionally substituted aralkyl and
R$^7$ represents furyl, tetrahydrofuryl, thiophenyl, or tetrahydrothiophenyl; isoxazolyl which is optionally substituted by alkyl; alkyl, alkenyl or alkynyl, in each case optionally substituted by cyano or thiocyano; dihalogenoalkyl or cycloalkyl; or the grouping —CH$_2$Az, —CH$_2$—OR$^8$, —CH$_2$—SR$^8$, —OR$^8$, —SR$^8$, —CH$_2$OSO$_2$R$^8$, —COOR$^8$ or

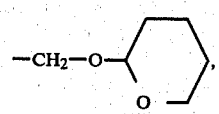

wherein
R$^8$ represents an optionally substituted alkyl, alkenyl, alkynyl or alkoxyalkyl radical and
Az represents pyrazol-1-yl, 1,2,4-triazol-1-yl or imidazol-1-yl.

The compounds of the formula (I) can exist in the syn-form or anti-form; they are predominantly obtained as mixtures of the two forms.

The invention also provides a process for the preparation of an N-oximinoalkyl-anilide of the formula (I), in which
(a) an anilinoalkyl oxime ether of the general formula

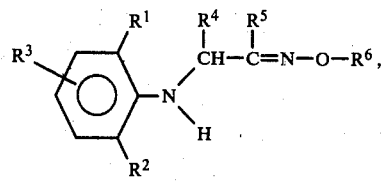
(II)

in which
R$^1$, R$^2$, R$^3$, R$^4$, R$^5$ and R$^6$ have the meanings indicated above,
is reacted with an acid chloride, bromide or anhydride of the general formula

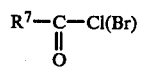
(IIIa)

or

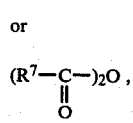
(IIIb)

in which
R$^7$ has the meaning indicated above,
in the presence of a diluent and if appropriate in the presence of an acid-binding agent, or
(b) an anilide of the general formula

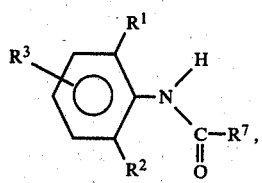
(IV)

in which
R$^1$, R$^2$, R$^3$ and R$^7$ have the meanings indicated above,
is reacted with a substituted oxime ether of the general formula

(V)

in which
R$^4$, R$^5$ and R$^6$ have the meanings indicated above and
Y represents halogen or the mesylate or tosylate radical,
in the presence of an acid-binding agent and if appropriate in the presence of a diluent, or
(c) an N-substituted anilide of the general formula

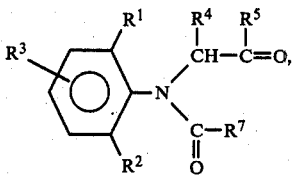
(VI)

in which
R$^1$, R$^2$, R$^3$, R$^4$, R$^5$ and R$^7$ have the meanings indicated above, is reacted with a salt of hydroxylamine or of a hydroxylamine derivative of the formula $$H_2N-O-R^6 \quad (VII),$$

in which
R$^6$ has the meaning indicated above,
in the presence of a diluent and in the presence of an acid-binding agent, or (d) an alkali metal salt or an oxime of the general formula

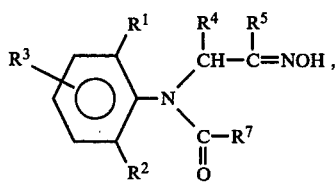

in which
R$^1$, R$^2$, R$^3$, R$^4$, R$^5$ and R$^7$ have the meanings indicated above,
is reacted with a compound of the general formula $$X-R^9 \quad (IX),$$

in which
R$^9$ represents alkyl, alkenyl, alkynyl, alkoxyalkyl, alkylthioalkyl or optionally substituted aralkyl and
X represents chlorine, bromine, mesyl, tosyl or methoxysulphonyloxy,
in the presence of an organic diluent or in the presence of an organic-aqueous two-phase system in the presence of a phase-transfer catalyst, the alkali metal salt of the oxime of the formula (VIII) being produced in situ, or (e) a halogenoacetanilide of the general formula

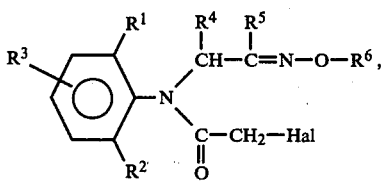

in which
R$^1$, R$^2$, R$^3$, R$^4$, R$^5$ and R$^6$ have the meanings indicated above and
Hal represents chlorine, bromine or iodine,
is reacted with a compound of the general formula $$B-R^{10} \quad (XI),$$

in which
B represents hydrogen or an alkali metal and R$^{10}$ represents Az or the grouping —OR$^8$ or —SR$^8$,
wherein
R$^8$ has the meaning indicated above,
in the presence of a diluent and if appropriate in the presence of an acid-binding agent, or (f) a hydroxyacetanilide of the general formula

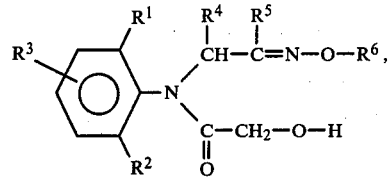

in which
R$^1$, R$^2$, R$^3$, R$^4$, R$^5$ and R$^6$ have the meanings indicated above, (1) is reacted, if appropriate after activation by means of an alkali metal, with a halide of the general formula $$Hal-R^{11} \quad (XIII),$$

in which
Hal has the meaning indicated above and
R$^{11}$ represents the radical R$^8$ or the grouping —SO$_2$R$^8$, wherein
R$^8$ has the meaning indicated above,
in the presence of a diluent and if appropriate in the presence of an acid-binding agent, or (2) is reacted with dihydropyran, of the formula

in the presence of a diluent and if appropriate in the presence of a catalyst.

The N-oximinoalkyl-anilides according to this invention have powerful fungicidal properties. Surprisingly, the compounds according to the invention exhibit a considerably more powerful action than the N-chloroacetyl-N-(2-ethyl-6-methylphenyl)-alanine ester known from the state of the art, which is a closely related compound chemically and from the point of view of its action. The substances according to the invention thus represent an enrichment of the art.

The formula (I) provides a general definition of the N-oximinoalkyl-anilides according to the invention. Preferably, in this formula,
R$^2$, R$^3$, R$^4$ and R$^5$ individually represent hydrogen or straight-chain or branched alkyl with 1 to 4 carbon atoms,
R$^1$ represents hydrogen, straight-chain or branched alkyl with 1 to 4 carbon atoms, fluorine, chlorine or bromine,
R$^6$ represents hydrogen, straight-chain or branched alkyl with 1 to 4 carbon atoms, alkenyl or alkynyl with in either case 2 to 4 carbon atoms, alkoxyalkyl or alkylthioalkyl with in either case 1 to 4 carbon atoms in the alkyl part and 1 to 4 carbon atoms in the alkoxy or alkylthio part, or optionally substituted aralkyl with 6 to 10 carbon atoms in the aryl part and 1 to 2 carbon atoms in the alkyl part (especially benzyl), each substituent being selected from halogen, straight-chain or branched alkyl with 1 to 4 carbon atoms, halogenoalkyl with 1 to 2 carbon atoms and 1 to 5 halogen atoms (preferred halogens being fluorine and chlorine), alkoxy with 1 to 2 carbon atoms, alkylthio with 1 to 2 carbon atoms, cyano and nitro.
R$^7$ represents furyl, tetrahydrofuryl, thiophenyl or tetrahydrothiophenyl; isoxazolyl which is optionally substituted by methyl or ethyl; alkyl with 1 to 4 carbon atoms or alkenyl or alkynyl with in either case 2 to 4 carbon atoms, in each case optionally substituted by cyano or thiocyano; dihalogenoalkyl with 1 to 2 carbon atoms (preferred halogen atoms being fluorine and chlorine); cycloalkyl with 3 to 7 carbon atoms; or the grouping —CH$_2$—Az, —CH$_2$—OR$^8$, —CH$_2$—SR$^8$, —OR$^8$, —SR$^8$, —CH$_2$—OSO$_2$R$^8$, —COOR$^8$ or

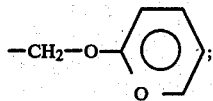

Az represents pyrazol-1-yl, 1,2,4-triazol-1-yl or imidazol-1-yl; and

R$^8$ represents alkyl with 1 to 4 carbon atoms or alkenyl or alkynyl with in either case 2 to 4 carbon atoms, in each case optionally substituted by halogen (especially fluorine, chlorine or bromine), cyano or thiocyano, or represents alkoxyalkyl with 1 to 4 carbon atoms in each alkyl part.

Very particularly preferred substituted N-oximinoalkyl-anilides of the formula (I) are those in which R$^1$ represents hydrogen, methyl, ethyl, isopropyl, sec.-butyl, tert.-butyl, chlorine or bromine; R$^2$ and R$^3$ represent hydrogen, methyl, ethyl, isopropyl, sec.-butyl or tert.-butyl; R$^4$ represents hydrogen, methyl or ethyl; R$^5$ represents hydrogen, methyl or ethyl; R$^6$ represents hydrogen, methyl, ethyl, isopropyl, n-propyl, n-butyl, sec.-butyl, tert.-butyl, vinyl, allyl, propargyl, methoxymethyl, ethoxymethyl, ethoxyethyl or methylthiomethyl, or benzyl which is optionally substituted by chlorine and/or methyl and/or methoxy and/or methylthio and/or trifluoromethyl; and R$^7$ represents 2-furyl, 2-thienyl, 2-tetrahydrofuryl, 5-methylisoxazol-3-yl, methoxymethyl, ethoxymethyl, allyloxymethyl, propargyloxymethyl, ethoxymethoxymethyl, methylmercaptomethyl, methoxy, ethoxy, methylmercapto, methylsulphonyloxymethyl, methoxycarbonyl, ethoxycarbonyl, dichloromethyl, cyclopropyl, cyclohexyl, pyrazol-1-yl-methyl, imidazol-1-yl-methyl, 1,2,4-triazol-1-yl-methyl or tetrahydropyran-2-yl-oxymethyl.

The following compounds of the general formula (I) may be mentioned specifically, in addition to the compounds mentioned later in the preparative examples:

| R$^1$ | R$^2$ | R$^3$ | R$^4$ | R$^5$ | R$^6$ | R$^7$ |
|---|---|---|---|---|---|---|
| CH$_3$ | CH$_3$ | H | H | H | H | —CH$_2$OCH$_3$ |
| CH$_3$ | CH$_3$ | H | H | H | H | 2-furyl |
| CH$_3$ | CH$_3$ | H | H | H | H | —CHCl$_2$ |
| CH$_3$ | CH$_3$ | H | H | H | H | —CO—O—CH$_3$ |
| CH$_3$ | CH$_3$ | H | H | H | H | —CH$_2$—N(1,2,4-triazol-1-yl) |
| CH$_3$ | CH$_3$ | H | H | H | H | cyclopropyl |
| CH$_3$ | CH$_3$ | H | H | H | H | —CH$_2$—N(imidazol-1-yl) |
| CH$_3$ | CH$_3$ | H | H | H | CH$_3$ | 2-furyl |
| CH$_3$ | CH$_3$ | H | H | H | CH$_3$ | —CHCl$_2$ |
| CH$_3$ | CH$_3$ | H | H | H | CH$_3$ | —CO—O—CH$_3$ |
| CH$_3$ | CH$_3$ | H | H | H | CH$_3$ | —CH$_2$—N(1,2,4-triazol-1-yl) |
| CH$_3$ | CH$_3$ | H | H | H | CH$_3$ | cyclopropyl |
| CH$_3$ | CH$_3$ | H | H | H | CH$_3$ | —CH$_2$—N(imidazol-1-yl) |
| CH$_3$ | CH$_3$ | H | H | H | C$_2$H$_5$ | 2-furyl |
| CH$_3$ | CH$_3$ | H | H | H | C$_2$H$_5$ | —CHCl$_2$ |
| CH$_3$ | CH$_3$ | H | H | H | C$_2$H$_5$ | —CO—O—CH$_3$ |

-continued

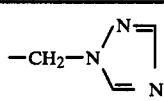

| R¹ | R² | R³ | R⁴ | R⁵ | R⁶ | R⁷ |
|---|---|---|---|---|---|---|
| CH₃ | CH₃ | H | H | H | C₂H₅ | −CH₂−N⟨triazole⟩ |
| CH₃ | CH₃ | H | H | H | C₂H₅ | ⟨cyclopropyl⟩ |
| CH₃ | CH₃ | H | H | H | C₂H₅ | −CH₂−N⟨imidazole⟩ |
| CH₃ | CH₃ | H | H | H | n-C₃H₇ | ⟨furyl⟩ |
| CH₃ | CH₃ | H | H | H | n-C₃H₇ | −CHCl₂ |
| CH₃ | CH₃ | H | H | H | n-C₃H₇ | −CO−O−CH₃ |
| CH₃ | CH₃ | H | H | H | n-C₃H₇ | −CH₂−N⟨triazole⟩ |
| CH₃ | CH₃ | H | H | H | n-C₃H₇ | ⟨cyclopropyl⟩ |
| CH₃ | CH₃ | H | H | H | n-C₃H₇ | −CH₂−N⟨imidazole⟩ |
| CH₃ | CH₃ | H | H | H | n-C₄H₉ | −CH₂OCH₃ |
| CH₃ | CH₃ | H | H | H | n-C₄H₉ | ⟨furyl⟩ |
| CH₃ | CH₃ | H | H | H | n-C₄H₉ | −CHCl₂ |
| CH₃ | CH₃ | H | H | H | n-C₄H₉ | −CO−O−CH₃ |
| CH₃ | CH₃ | H | H | H | n-C₄H₉ | −CH₂−N⟨triazole⟩ |
| CH₃ | CH₃ | H | H | H | n-C₄H₉ | ⟨cyclopropyl⟩ |
| CH₃ | CH₃ | H | H | H | n-C₄H₉ | −CH₂−N⟨imidazole⟩ |
| CH₃ | CH₃ | H | H | CH₃ | H | −CHCl₂ |
| CH₃ | CH₃ | H | H | CH₃ | H | −CO−O−CH₃ |
| CH₃ | CH₃ | H | H | CH₃ | H | −CH₂−N⟨triazole⟩ |
| CH₃ | CH₃ | H | H | CH₃ | H | ⟨cyclopropyl⟩ |
| CH₃ | CH₃ | H | H | CH₃ | H | −CH₂−N⟨imidazole⟩ |
| CH₃ | CH₃ | H | H | CH₃ | CH₃ | ⟨furyl⟩ |
| CH₃ | CH₃ | H | H | CH₃ | CH₃ | −CHCl₂ |
| CH₃ | CH₃ | H | H | CH₃ | CH₃ | −CO−O−CH₃ |
| CH₃ | CH₃ | H | H | CH₃ | CH₃ | −CH₂−N⟨triazole⟩ |

-continued $$\begin{array}{c} R^1 \quad R^4 \quad R^5 \\ R^3 - \underset{R^2}{\underset{|}{C_6H_3}} - \underset{\underset{O}{\overset{|}{C}-R^7}}{N} - CH - C = N - O - R^6 \end{array} \quad (I)$$

| R¹ | R² | R³ | R⁴ | R⁵ | R⁶ | R⁷ |
|---|---|---|---|---|---|---|
| CH₃ | CH₃ | H | H | CH₃ | CH₃ |  |
| CH₃ | CH₃ | H | H | CH₃ | CH₃ | —CH₂—N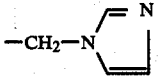 |
| CH₃ | CH₃ | H | H | CH₃ | C₂H₅ | —CH₂OCH₂ |
| CH₃ | CH₃ | H | H | CH₃ | C₂H₅ |  |
| CH₃ | CH₃ | H | H | CH₃ | C₂H₅ | —CHCl₂ |
| CH₃ | CH₃ | H | H | CH₃ | C₂H₅ | —CO—O—CH₃ |
| CH₃ | CH₃ | H | H | CH₃ | C₂H₅ | —CH₂—N |
| CH₃ | CH₃ | H | H | CH₃ | C₂H₅ |  |
| CH₃ | CH₃ | H | H | CH₃ | C₂H₅ | —CH₂—N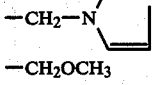 |
| CH₃ | CH₃ | H | H | CH₃ | n-C₃H₇ | —CH₂OCH₃ |
| CH₃ | CH₃ | H | H | CH₃ | n-C₃H₇ |  |
| CH₃ | CH₃ | H | H | CH₃ | n-C₃H₇ | —CHCl₂ |
| CH₃ | CH₃ | H | H | CH₃ | n-C₃H₇ | —CO—O—CH₃ |
| CH₃ | CH₃ | H | H | CH₃ | n-C₃H₇ | —CH₂—N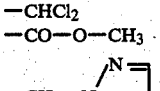 |
| CH₃ | CH₃ | H | H | CH₃ | n-C₃H₇ |  |
| CH₃ | CH₃ | H | H | CH₃ | n-C₃H₇ | —CH₂—N |
| CH₃ | CH₃ | H | H | CH₃ | n-C₄H₉ | —CH₂OCH₃ |
| CH₃ | CH₃ | H | H | CH₃ | n-C₄H₉ |  |
| CH₃ | CH₃ | H | H | CH₃ | n-C₄H₉ | —CHCl₂ |
| CH₃ | CH₃ | H | H | CH₃ | n-C₄H₉ | —CO—O—CH₃ |
| CH₃ | CH₃ | H | H | CH₃ | n-C₄H₉ | —CH₂—N |
| CH₃ | CH₃ | H | H | CH₃ | n-C₄H₉ | 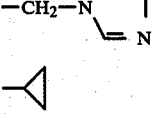 |
| CH₃ | CH₃ | H | H | CH₃ | n-C₄H₉ | —CH₂—N |
| CH₃ | CH₃ | H | CH₃ | H | H | —CH₂OCH₃ |
| CH₃ | CH₃ | H | CH₃ | H | H |  |
| CH₃ | CH₃ | H | CH₃ | H | H | —CHCl₂ |
| CH₃ | CH₃ | H | CH₃ | H | H | —CO—O—CH₃ |

-continued $$\underset{\underset{\underset{O}{\overset{|}{C}-R^7}}{\overset{R^3}{\underset{R^2}{\bigcirc}}\!\!\!\!\!\!\!\!\!\!\!\!\!\overset{R^1}{\underset{|}{N}}}}{\overset{R^4}{\underset{|}{C}H}-\overset{R^5}{\underset{|}{C}}=N-O-R^6} \quad (I)$$

| R¹ | R² | R³ | R⁴ | R⁵ | R⁶ | R⁷ |
|---|---|---|---|---|---|---|
| CH₃ | CH₃ | H | CH₃ | H | H | —CH₂—N(triazole) |
| CH₃ | CH₃ | H | CH₃ | H | H | cyclopropyl |
| CH₃ | CH₃ | H | CH₃ | H | H | —CH₂—N(imidazole) |
| CH₃ | CH₃ | H | CH₃ | H | CH₃ | —CH₂—N(triazole) |
| CH₃ | CH₃ | H | CH₃ | H | CH₃ | cyclopropyl |
| CH₃ | CH₃ | H | CH₃ | H | C₂H₅ | furyl |
| CH₃ | CH₃ | H | CH₃ | H | C₂H₅ | —CH₂—N(triazole) |
| CH₃ | CH₃ | H | CH₃ | H | C₂H₅ | cyclopropyl |
| CH₃ | CH₃ | H | CH₃ | H | n-C₃H₇ | —CH₂OCH₃ |
| CH₃ | CH₃ | H | CH₃ | H | n-C₃H₇ | furyl |
| CH₃ | CH₃ | H | CH₃ | H | n-C₃H₇ | —CHCl₂ |
| CH₃ | CH₃ | H | CH₃ | H | n-C₃H₇ | —CO—O—CH₃ |
| CH₃ | CH₃ | H | CH₃ | H | n-C₃H₇ | —CH₂—N(triazole) |
| CH₃ | CH₃ | H | CH₃ | H | n-C₃H₇ | cyclopropyl |
| CH₃ | CH₃ | H | CH₃ | H | n-C₃H₇ | —CH₂—N(triazole) |
| CH₃ | CH₃ | H | CH₃ | H | n-C₄H₉ | —CH₂OCH₃ |
| CH₃ | CH₃ | H | CH₃ | H | n-C₄H₉ | furyl |
| CH₃ | CH₃ | H | CH₃ | H | n-C₄H₉ | —CHCl₂ |
| CH₃ | CH₃ | H | CH₃ | H | n-C₄H₉ | —CO—O—CH₃ |
| CH₃ | CH₃ | H | CH₃ | H | n-C₄H₉ | —CH₂—N(triazole) |
| CH₃ | CH₃ | H | CH₃ | H | n-C₄H₉ | cyclopropyl |
| CH₃ | CH₃ | H | CH₃ | H | n-C₄H₉ | —CH₂—N(imidazole) |
| CH₃ | CH₃ | H | CH₃ | CH₃ | H | —CH₂OCH₃ |
| CH₃ | CH₃ | H | CH₃ | CH₃ | H | furyl |
| CH₃ | CH₃ | H | CH₃ | CH₃ | H | —CHCl₂ |

-continued $$\begin{array}{c} R^1 \quad R^4 \quad R^5 \\ R^3 \diagdown \diagup CH-C=N-O-R^6 \\ \phantom{R^3}\diagup N \\ \phantom{R^3}| \\ \phantom{R^3}C-R^7 \\ \phantom{R^3}\| \\ \phantom{R^3}O \\ R^2 \end{array} \quad (I)$$

| R¹ | R² | R³ | R⁴ | R⁵ | R⁶ | R⁷ |
|---|---|---|---|---|---|---|
| CH₃ | CH₃ | H | CH₃ | CH₃ | H | —CO—O—CH₃ |
| CH₃ | CH₃ | H | CH₃ | CH₃ | H | —CH₂—N(triazolyl) |
| CH₃ | CH₃ | H | CH₃ | CH₃ | H | cyclopropyl |
| CH₃ | CH₃ | H | CH₃ | CH₃ | H | —CH₂—N(imidazolyl) |
| CH₃ | CH₃ | H | CH₃ | CH₃ | CH₃ | cyclopropyl |
| CH₃ | CH₃ | H | CH₃ | CH₃ | C₂H₅ | —CH₂OCH₃ |
| CH₃ | CH₃ | H | CH₃ | CH₃ | C₂H₅ | furyl |
| CH₃ | CH₃ | H | CH₃ | CH₃ | C₂H₅ | —CHCl₂ |
| CH₃ | CH₃ | H | CH₃ | CH₃ | C₂H₅ | —CO—O—CH₃ |
| CH₃ | CH₃ | H | CH₃ | CH₃ | C₂H₅ | —CH₂—N(triazolyl) |
| CH₃ | CH₃ | H | CH₃ | CH₃ | C₂H₅ | cyclopropyl |
| CH₃ | CH₃ | H | CH₃ | CH₃ | C₂H₅ | —CH₂—N(imidazolyl) |
| CH₃ | CH₃ | H | CH₃ | CH₃ | n-C₃H₇ | —CH₂OCH₃ |
| CH₃ | CH₃ | H | CH₃ | CH₃ | n-C₃H₇ | furyl |
| CH₃ | CH₃ | H | CH₃ | CH₃ | n-C₃H₇ | —CHCl₂ |
| CH₃ | CH₃ | H | CH₃ | CH₃ | n-C₃H₇ | —CO—O—CH₃ |
| CH₃ | CH₃ | H | CH₃ | CH₃ | n-C₃H₇ | —CH₂—O—N(triazolyl) |
| CH₃ | CH₃ | H | CH₃ | CH₃ | n-C₃H₇ | cyclopropyl |
| CH₃ | CH₃ | H | CH₃ | CH₃ | n-C₃H₇ | —CH₂—N(imidazolyl) |
| CH₃ | CH₃ | H | CH₃ | CH₃ | n-C₄H₉ | —CH₂OCH₃ |
| CH₃ | CH₃ | H | CH₃ | CH₃ | n-C₄H₉ | furyl |
| CH₃ | CH₃ | H | CH₃ | CH₃ | n-C₄H₉ | —CHCl₂ |
| CH₃ | CH₃ | H | CH₃ | CH₃ | n-C₄H₉ | —CO—O—CH₃ |
| CH₃ | CH₃ | H | CH₃ | CH₃ | n-C₄H₉ | —CH₂—N(triazolyl) |
| CH₃ | CH₃ | H | CH₃ | CH₃ | n-C₄H₉ | cyclopropyl |
| CH₃ | CH₃ | H | CH₃ | CH₃ | n-C₄H₉ | —CH₂—N(imidazolyl) |

-continued $$\begin{array}{c} R^3 \underset{R^2}{\overset{R^1}{\bigcirc}} N \underset{\underset{O}{\overset{|}{C}}-R^7}{\overset{CH-C=N-O-R^6}{\overset{|}{\phantom{X}}\overset{|}{\phantom{X}}}} \end{array} \quad (I)$$

| $R^1$ | $R^2$ | $R^3$ | $R^4$ | $R^5$ | $R^6$ | $R^7$ |
|---|---|---|---|---|---|---|
| CH₃ | CH₃ | H | CH₃ | CH₃ | CH₃ | $-CH_2-N\underset{N=}{\overset{=N}{\diagdown}}$ |
| CH₃ | CH₃ | H | CH₃ | CH₃ | CH₃ | —COOCH₃ |
| C₂H₅ | C₂H₅ | H | CH₃ | H | CH₃ | —CH₂OCH₃ |
| CH₃ | CH₃ | H | CH₃ | H | CH₃ | $-CH_2-N\underset{N}{\overset{=N}{\diagdown}}$ |
| CH₃ | CH₃ | H | H | CH₃ | —CH₂—CH=CH₂ | —CH₂OCH₃ |
| CH₃ | CH₃ | H | H | CH₃ | —CH₂—C≡CH | —CH₂OCH₃ |
| CH₃ | CH₃ | H | H | CH₃ | —CH₂—CH=CH₂ | furan-2-yl |
| CH₃ | CH₃ | H | H | CH₃ | —CH₂—C₆H₅ | —CH₂OCH₃ |
| CH₃ | CH₃ | H | CH₃ | CH₃ | CH₃ | $-CH_2-N\underset{N}{\overset{=N}{\diagdown}}$ |
| Cl | CH₃ | H | H | CH₃ | CH₃ | —CH₂OCH₃ |
| Cl | CH₃ | H | H | CH₃ | CH₃ | furan-2-yl |
| CH₃ | CH₃ | H | H | H | CH₃ | —CH₂OCH₂—C≡CH |
| CH₃ | CH₃ | H | H | H | CH₃ | —CH₂OCH₂—CH=CH₂ |
| Cl | CH₃ | H | CH₃ | H | CH₃ | —CH₂OCH₃ |

If, for example, 2,6-dimethylanilinomethyl methyl ketoxime methyl ether and methoxyacetic acid chloride are used as starting substances in process variant (a), the course of the reaction can be represented by the following equation:

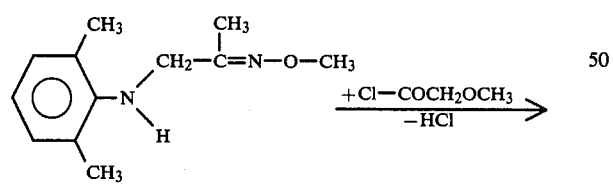

If, for example, 2,6-dimethyl-N-(2-furoyl)-aniline and chloromethylaldoxime methyl ether are used as starting substances in process variant (b), the course of the reaction can be represented by the following equation:

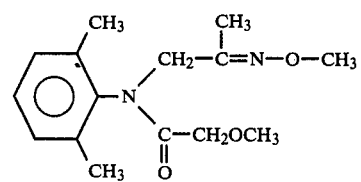

If, for example, 2,6-dimethyl-N-acetonyl-methoxyacetanilide and O-methyl-hydroxylamine are used as starting substances in process variant (c), the course of the reaction can be represented by the following equation:

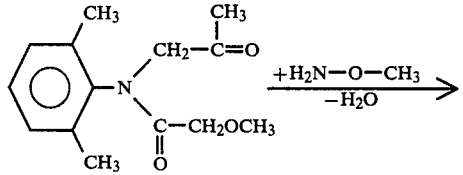

-continued

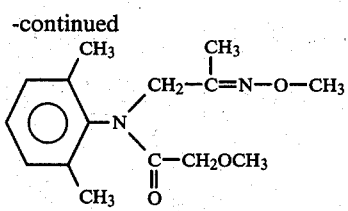

If, for example, the sodium salt of 2,6-dimethylmethoxyacetanilido-methyl methyl ketoxime and benzyl chloride are used as starting substances in process variant (d), the course of the reaction can be represented by the following equation:

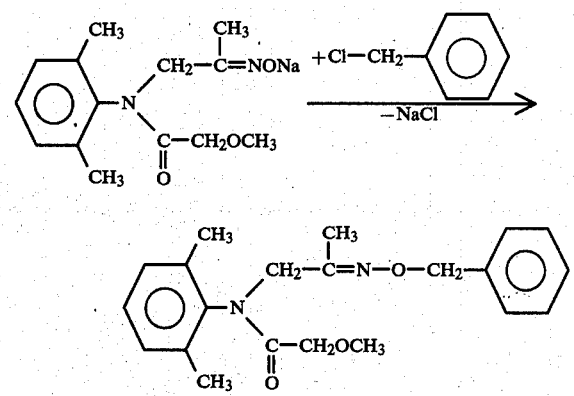

If, for example, 2,6-dimethyl-N-(2'-methoxyiminoethyl)-chloroacetanilide and 1,2,4-triazole are used as starting substances in process variant (e), the course of the reaction can be represented by the following equation:

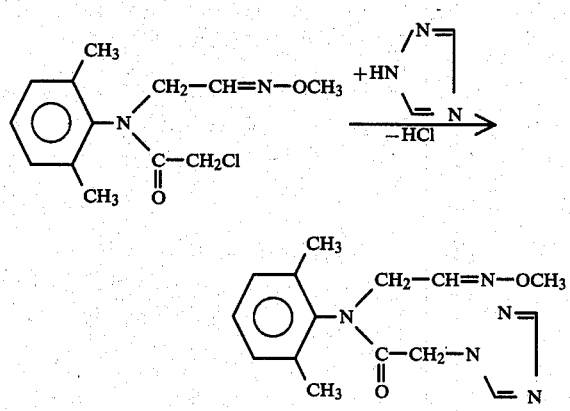

If, for example, 2,6-dimethyl-N-(2'-methoxyiminoethyl)-hydroxyacetanilide and ethoxymethyl chloride are used as starting substances in process variant (f)(1), the course of the reaction can be represented by the following equation:

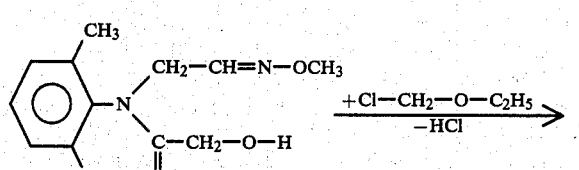

-continued

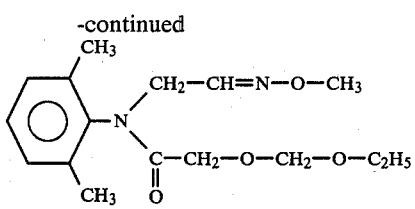

If, for example, 2,6-dimethyl-N-(2'-methoxyiminoethyl)-hydroxy-acetanilide and 3,4-dihydro-2H-pyran are used as starting substances in process variant (f)(2), the course of the reaction can be represented by the following equation:

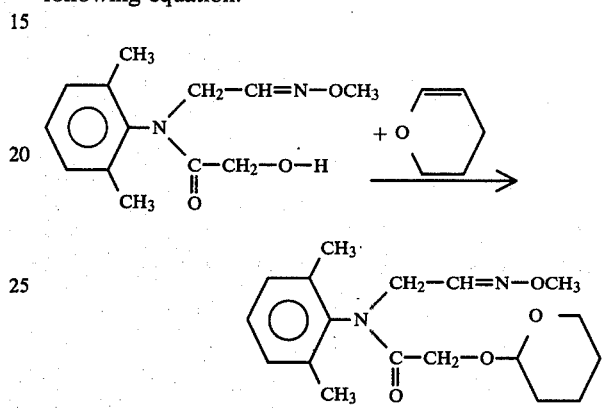

The formula (II) provides a general definition of the anilinoalkyl oxime ethers required as starting substances in carrying out process variant (a). In this formula, $R^1$, $R^2$, $R^3$, $R^4$, $R^5$ and $R^6$ preferably have those meanings which have already been mentioned as preferred in connection with the description of the substances of the formula (I).

The following compounds may be mentioned as specific examples of compounds of the formula (II):

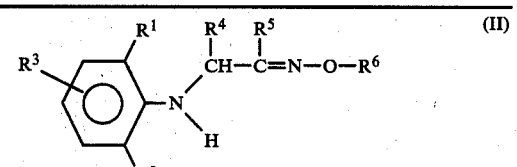

| $R^1$ | $R^2$ | $R^3$ | $R^4$ | $R^5$ | $R^6$ |
|---|---|---|---|---|---|
| H | H | H | H | H | H |
| $CH_3$ | $CH_3$ | H | H | H | H |
| $CH_3$ | $C_2H_5$ | H | H | H | H |
| $C_2H_5$ | $C_2H_5$ | H | H | H | H |
| $CH_3$ | $CH_3$ | H | H | H | $CH_3$ |
| $CH_3$ | $C_2H_5$ | H | H | H | $CH_3$ |
| $C_2H_5$ | $C_2H_5$ | H | H | H | $CH_3$ |
| $C_2H_5$ | H | H | H | H | $CH_3$ |
| $C(CH_3)_3$ | H | H | H | H | $CH_3$ |
| Cl | $CH_3$ | H | H | H | $CH_3$ |
| Br | $CH_3$ | H | H | H | $CH_3$ |
| Cl | $C(CH_3)_3$ | H | H | H | $CH_3$ |
| $CH_3$ | H | 3-$CH_3$ | H | H | $CH_3$ |
| i-$C_3H_7$ | $C_2H_5$ | H | H | H | $CH_3$ |
| $CH_3$ | H | H | H | H | $CH_3$ |
| $CH_3$ | $CH_3$ | H | H | H | $C_2H_5$ |
| $CH_3$ | $C_2H_5$ | H | H | H | $C_2H_5$ |
| $C_2H_5$ | $C_2H_5$ | H | H | H | $C_2H_5$ |
| $C_2H_5$ | H | H | H | H | $C_2H_5$ |
| $C(CH_3)_3$ | H | H | H | H | $C_2H_5$ |
| Cl | $CH_3$ | H | H | H | $C_2H_5$ |
| Br | $CH_3$ | H | H | H | $C_2H_5$ |
| Cl | $C(CH_3)_3$ | H | H | H | $C_2H_5$ |
| $CH_3$ | H | 3-$CH_3$ | H | H | $C_2H_5$ |

-continued

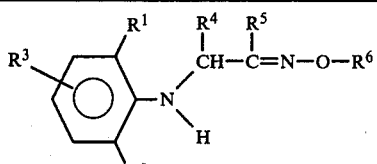

(II)

| R¹ | R² | R³ | R⁴ | R⁵ | R⁶ |
|---|---|---|---|---|---|
| i-C₃H₇ | C₂H₅ | H | H | H | C₂H₅ |
| CH₃ | H | H | H | H | C₂H₅ |
| CH₃ | CH₃ | H | H | H | n-C₃H₇ |
| CH₃ | C₂H₅ | H | H | H | n-C₃H₇ |
| C₂H₅ | C₂H₅ | H | H | H | n-C₃H₇ |
| C(CH₃)₃ | H | H | H | H | n-C₃H₇ |
| CH₃ | CH₃ | H | H | H | n-C₄H₉ |
| CH₃ | C₂H₅ | H | H | H | n-C₄H₉ |
| C₂H₅ | C₂H₅ | H | H | H | n-C₄H₉ |
| C(CH₃)₃ | H | H | H | H | n-C₄H₉ |
| CH₃ | CH₃ | H | CH₃ | H | —CH₂—CH=CH₂ |
| CH₃ | C₂H₅ | H | CH₃ | H | —CH₂—CH=CH₂ |
| C₂H₅ | C₂H₅ | H | CH₃ | H | —CH₂—CH=CH₂ |
| C(CH₃)₃ | H | H | CH₃ | H | —CH₂—CH=CH₂ |
| CH₃ | CH₃ | H | CH₃ | H | —CH₂—C≡CH |
| CH₃ | C₂H₅ | H | CH₃ | H | —CH₂—C≡CH |
| C₂H₅ | C₂H₅ | H | CH₃ | H | —CH₂—C≡CH |
| C(CH₃)₃ | H | H | CH₃ | H | —CH₂—C≡CH |
| CH₃ | CH₃ | H | CH₃ | H | —CH₂—O—CH₃ |
| CH₃ | C₂H₅ | H | CH₃ | H | —CH₂—O—CH₃ |
| C₂H₅ | C₂H₅ | H | CH₃ | H | —CH₂—O—CH₃ |
| C(CH₃)₃ | H | H | CH₃ | H | —CH₂—O—CH₃ |
| CH₃ | CH₃ | H | CH₃ | H | —CH₂—⌬ |
| CH₃ | C₂H₅ | H | CH₃ | H | —CH₂—⌬ |
| C₂H₅ | C₂H₅ | H | CH₃ | H | —CH₂—⌬ |
| C(CH₃)₃ | H | H | CH₃ | H | —CH₂—⌬ |
| CH₃ | CH₃ | H | CH₃ | CH₃ | CH₃ |
| CH₃ | C₂H₅ | H | CH₃ | CH₃ | CH₃ |
| C₂H₅ | C₂H₅ | H | CH₃ | CH₃ | CH₃ |
| C(CH₃)₃ | H | H | CH₃ | CH₃ | CH₃ |
| CH₃ | CH₃ | H | CH₃ | CH₃ | C₂H₅ |
| CH₃ | C₂H₅ | H | CH₃ | CH₃ | C₂H₅ |
| C₂H₅ | C₂H₅ | H | CH₃ | CH₃ | C₂H₅ |
| C(CH₃)₃ | H | H | CH₃ | CH₃ | C₂H₅ |
| CH₃ | CH₃ | H | CH₃ | CH₃ | n-C₃H₇ |
| CH₃ | C₂H₅ | H | CH₃ | CH₃ | n-C₃H₇ |
| C₂H₅ | C₂H₅ | H | CH₃ | CH₃ | n-C₃H₇ |
| C(CH₃)₃ | H | H | CH₃ | CH₃ | n-C₃H₇ |
| CH₃ | CH₃ | H | CH₃ | CH₃ | n-C₄H₉ |
| CH₃ | C₂H₅ | H | CH₃ | CH₃ | n-C₄H₉ |
| C₂H₅ | C₂H₅ | H | CH₃ | CH₃ | n-C₄H₉ |
| C(CH₃)₃ | H | H | CH₃ | CH₃ | n-C₄H₉ |
| CH₃ | CH₃ | H | H | H | CH₃ |
| CH₃ | C₂H₅ | H | H | H | CH₃ |
| C₂H₅ | C₂H₅ | H | H | H | CH₃ |
| C(CH₃)₃ | H | H | H | H | CH₃ |
| CH₃ | CH₃ | H | H | H | C₂H₅ |
| CH₃ | C₂H₅ | H | H | H | C₂H₅ |
| C₂H₅ | C₂H₅ | H | H | H | C₂H₅ |
| C(CH₃)₃ | H | H | H | H | C₂H₅ |
| CH₃ | CH₃ | H | H | H | n-C₃H₇ |
| CH₃ | C₂H₅ | H | H | H | n-C₃H₇ |
| C₂H₅ | C₂H₅ | H | H | H | n-C₃H₇ |
| C(CH₃)₃ | H | H | H | H | n-C₃H₇ |
| CH₃ | CH₃ | H | H | H | n-C₄H₉ |
| CH₃ | C₂H₅ | H | H | H | n-C₄H₉ |
| C₂H₅ | C₂H₅ | H | H | H | n-C₄H₉ |
| C(CH₃)₃ | H | H | H | H | n-C₄H₉ |
| CH₃ | CH₃ | H | CH₃ | CH₃ | —CH₂—CH=CH₂ |
| CH₃ | C₂H₅ | H | CH₃ | CH₃ | —CH₂—CH=CH₂ |
| C₂H₅ | C₂H₅ | H | CH₃ | CH₃ | —CH₂—CH=CH₂ |
| C(CH₃)₃ | H | H | CH₃ | CH₃ | —CH₂—CH=CH₂ |
| CH₃ | CH₃ | H | CH₃ | CH₃ | —CH₂—C≡CH |
| CH₃ | C₂H₅ | H | CH₃ | CH₃ | —CH₂—C≡CH |

-continued

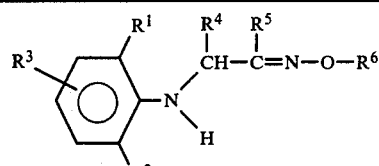

(II)

| R¹ | R² | R³ | R⁴ | R⁵ | R⁶ |
|---|---|---|---|---|---|
| C₂H₅ | C₂H₅ | H | CH₃ | CH₃ | —CH₂—C≡CH |
| C(CH₃)₃ | H | H | CH₃ | CH₃ | —CH₂—C≡CH |
| CH₃ | CH₃ | H | CH₃ | CH₃ | —CH₂OCH₃ |
| CH₃ | C₂H₅ | H | CH₃ | CH₃ | —CH₂OCH₃ |
| C₂H₅ | C₂H₅ | H | CH₃ | CH₃ | —CH₃OCH₃ |
| C(CH₃)₃ | H | H | CH₃ | CH₃ | —CH₂OCH₃ |
| CH₃ | CH₃ | H | CH₃ | CH₃ | —CH₂—⌬ |
| CH₃ | C₂H₅ | H | CH₃ | CH₃ | —CH₂—⌬ |
| C₂H₅ | C₂H₅ | H | CH₃ | CH₃ | —CH₂—⌬ |
| C(CH₃)₃ | H | H | CH₃ | CH₃ | —CH₂—⌬ |

The anilinoalkyl oxime ethers of the formula (II) have not hitherto been disclosed in the literature. However, they are described in U.S. Ser. No. 086,111, filed Oct. 10, 1979, now abandoned. According to this earlier application, they can be obtained, for example, by reacting anilines of the general formula $$\text{(XV)}$$

in which

R¹, R² and R³ have the meanings indicated above, with substituted oxime ethers of the general formula $$Y-\underset{R^4}{\overset{|}{C}}H-\underset{R^5}{\overset{|}{C}}=N-O-R^6, \quad \text{(V)}$$

in which

R⁴, R⁵, R⁶ and Y have the meanings indicated above, in the presence of an acid-binding agent, for example an alkali metal carbonate, and if appropriate in the presence of an inert organic solvent, for example toluene or dimethylformamide, at a temperature between 20° and 160° C.

The anilines of the formula (XV) required as starting substances are generally known compounds of organic chemistry. Examples which may be mentioned are: aniline, 2-methylaniline, 2-ethylaniline, 2-isopropylaniline, 2-sec.-butylaniline, 2-tert.-butylaniline, 2,6-dimethylaniline, 2,3-dimethylaniline, 2,5-dimethylaniline, 3,5-dimethylaniline, 2,6-diethylaniline, 2-ethyl-6-methylaniline, 2,3,4-trimethylaniline, 2,4,6-trimethylaniline, 2,4,5-trimethylaniline, 2-ethyl-4,6-dimethylaniline, 2,6-diethyl-4-methylaniline, 2,6-diisopropyl-4-methylaniline, 2,3,5-trimethylaniline, 2,3,6-trimethylaniline, 6-chloro-2-methylaniline, 2-bromo-6-methylaniline and 2-chloro-6-tert.-butylaniline.

Substituted oxime ethers of the formula (V) required as starting substances are known from U.S. Pat. No. 3,896,189 and J.Org.Chem. 36, (1971), 3,467, and they can easily be prepared by the processes indicated in these references (see the appropriate general statements in respect of process variant (b)).

The formulae (IIIa) and (IIIb) provide general definitions of the acid chlorides, bromides and anhydrides also to be used as starting substances for process variant (a). In these formulae, $R^7$ preferably has those meanings which have already been mentioned as preferred in connection with the description of the substances of the formula (I).

The acid chlorides, bromides and anhydrides of the formulae (IIIa) and (IIIb) are generally known compounds of organic chemistry.

The formula (IV) provides a general definition of the anilides required as starting substances in carrying out process variant (b). In this formula, $R^1$, $R^2$, $R^3$ and $R^7$ preferably have those meanings which have already been mentioned as preferred in connection with the description of the substances of the formula (I).

The anilides of the formula (IV) can be obtained in a generally known manner, by reacting corresponding anilines with an acid chloride, bromide or anhydride of the formula (IIIa) or (IIIb) in the presence of an inert organic solvent, for example toluene or methylene chloride, if appropriate in the presence of an acid-binding agent, for example potassium carbonate or triethylamine, or in the presence of a catalyst, for example dimethylformamide, at a temperature between 0° and 100° C., analogously to the conditions of process variant (a).

Examples of starting substances of the formula (IV) which may be mentioned are:

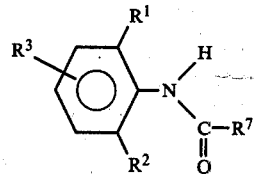
(IV)

| $R^1$ | $R^2$ | $R^3$ | $R^7$ |
|---|---|---|---|
| CH$_3$ | CH$_3$ | H | —CH$_2$OCH$_3$ |
| CH$_3$ | C$_2$H$_5$ | H | —CH$_2$OCH$_3$ |
| C$_2$H$_5$ | C$_2$H$_5$ | H | —CH$_2$OCH$_3$ |
| CH$_3$ | CH$_3$ | 3-CH$_3$ | —CH$_2$OCH$_3$ |
| Cl | CH$_3$ | H | —CH$_2$OCH$_3$ |
| CH$_3$ | CH$_3$ | H | ![furfuryl] |
| CH$_3$ | C$_2$H$_5$ | H | ![furfuryl] |
| C$_2$H$_5$ | C$_2$H$_5$ | H | ![furfuryl] |
| CH$_3$ | CH$_3$ | 3-CH$_3$ | ![furfuryl] |
| Cl | CH$_3$ | H | ![furfuryl] |
| CH$_3$ | CH$_3$ | H | —COOCH$_3$ |
| CH$_3$ | C$_2$H$_5$ | H | —COOCH$_3$ |
| C$_2$H$_5$ | C$_2$H$_5$ | H | —COOCH$_3$ |

-continued

| $R^1$ | $R^2$ | $R^3$ | $R^7$ |
|---|---|---|---|
| CH$_3$ | CH$_3$ | 3-CH$_3$ | —COOCH$_3$ |
| Cl | CH$_3$ | H | —COOCH$_3$ |
| CH$_3$ | CH$_3$ | H | —CH$_2$—N(pyrazol) |
| CH$_3$ | C$_2$H$_5$ | H | —CH$_2$—N(pyrazol) |
| C$_2$H$_5$ | C$_2$H$_5$ | H | —CH$_2$—N(pyrazol) |
| CH$_3$ | CH$_3$ | 3-CH$_3$ | —CH$_2$—N(pyrazol) |
| Cl | CH$_3$ | H | —CH$_2$—N(pyrazol) |
| CH$_3$ | CH$_3$ | H | —CH$_2$—N(imidazol) |
| CH$_3$ | C$_2$H$_5$ | H | —CH$_2$—N(imidazol) |
| C$_2$H$_5$ | C$_2$H$_5$ | H | —CH$_2$—N(imidazol) |
| CH$_3$ | CH$_3$ | 3-CH$_3$ | —CH$_2$—N(imidazol) |
| Cl | CH$_3$ | H | —CH$_2$—N(imidazol) |
| CH$_3$ | CH$_3$ | H | —CH$_2$—N(pyrrol) |
| CH$_3$ | C$_2$H$_5$ | H | —CH$_2$—N(pyrrol) |
| C$_2$H$_5$ | C$_2$H$_5$ | H | —CH$_2$—N(pyrrol) |
| CH$_3$ | CH$_3$ | 3-CH$_3$ | —CH$_2$—N(pyrrol) |
| Cl | CH$_3$ | H | —CH$_2$—N(pyrrol) |
| CH$_3$ | CH$_3$ | H | —CH$_2$—O—SO$_2$CH$_3$ |
| CH$_3$ | C$_2$H$_5$ | H | —CH$_2$—O—SO$_2$CH$_3$ |
| C$_2$H$_5$ | C$_2$H$_5$ | H | —CH$_2$—O—SO$_2$CH$_3$ |
| CH$_3$ | CH$_3$ | 3-CH$_3$ | —CH$_2$—O—SO$_2$CH$_3$ |
| Cl | CH$_3$ | H | —CH$_2$—O—SO$_2$CH$_3$ |
| CH$_3$ | CH$_3$ | H | —CHCl$_2$ |

-continued

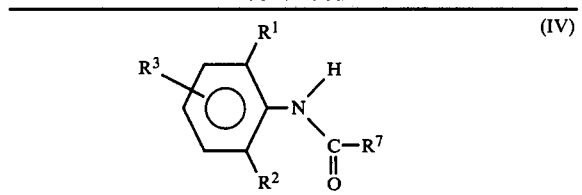

(IV)

| R¹ | R² | R³ | R⁷ |
|---|---|---|---|
| CH₃ | C₂H₅ | H | —CHCl₂ |
| C₂H₅ | C₂H₅ | H | —CHCl₂ |
| CH₃ | CH₃ | 3-CH₃ | —CHCl₂ |
| Cl | CH₃ | H | —CHCl₂ |
| CH₃ | CH₃ | H | ▷ |
| CH₃ | C₂H₅ | H | ▷ |
| C₂H₅ | C₂H₅ | H | ▷ |
| CH₃ | CH₃ | 3-CH₃ | ▷ |
| Cl | CH₃ | H | ▷ |
| CH₃ | CH₃ | H | —OC₂H₅ |
| CH₃ | C₂H₅ | H | —OC₂H₅ |
| C₂H₅ | C₂H₅ | H | —OC₂H₅ |
| CH₃ | CH₃ | 3-CH₃ | —OC₂H₅ |
| Cl | CH₃ | H | —OC₂H₅ |
| CH₃ | CH₃ | H | tetrahydrofuryl |
| CH₃ | C₂H₅ | H | tetrahydrofuryl |
| C₂H₅ | C₂H₅ | H | tetrahydrofuryl |
| CH₃ | CH₃ | 3-CH₃ | tetrahydrofuryl |
| Cl | CH₃ | H | tetrahydrofuryl |
| CH₃ | CH₃ | H | —CH₂—O—CH₂—O—C₂H₅ |
| CH₃ | C₂H₅ | H | —CH₂—O—CH₂—O—C₂H₅ |
| C₂H₅ | C₂H₅ | H | —CH₂—O—CH₂—O—C₂H₅ |
| CH₃ | CH₃ | 3-CH₃ | —CH₂—O—CH₂—O—C₂H₅ |
| Cl | CH₃ | H | —CH₂—O—CH₂—O—C₂H₅ |
| CH₃ | CH₃ | H | —CH₂—O—(tetrahydropyranyl) |
| CH₃ | C₂H₅ | H | —CH₂—O—(tetrahydropyranyl) |

-continued

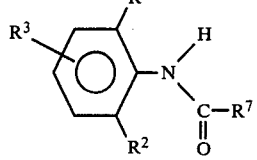

(IV)

| R¹ | R² | R³ | R⁷ |
|---|---|---|---|
| C₂H₅ | C₂H₅ | H | —CH₂—O—(tetrahydropyranyl) |
| CH₃ | CH₃ | 3-CH₃ | —CH₂—O—(tetrahydropyranyl) |
| Cl | CH₃ | H | —CH₂—O—(tetrahydropyranyl) |

The formula (V) provides a general definition of the substituted oxime ethers also to be used as starting substances for process variant (b). In this formula, $R^4$, $R^5$ and $R^6$ preferably have those meanings which have already been mentioned as preferred in connection with the description of the substances of the formula (I). Y preferably represents chlorine, bromine or the mesylate or tosylate radical.

The substituted oxime ethers of the formula (V) are known (see, for example, U.S. Pat. No. 3,896,189); they can be obtained in a generally known manner, by reacting corresponding carbonyl compounds with hydroxylamine (derivatives) in the presence of a solvent, preferably an alcohol, at temperatures between 20° C. and 100° C., preferably between 50° C. and 80° C. The hydroxylamine (derivative) is preferably employed in the form of a salt, especially as the hydrochloride, and if appropriate in the presence of an acid-binding agent, for example sodium acetate. Isolation of the end products is effected in the customary manner. The substituted oxime ethers of the formula (V) can also be obtained if oxime ethers of the general formula $$R^4-CH_2-\overset{R^5}{\underset{|}{C}}=N-O-R^6, \quad (Va)$$

in which $R^4$, $R^5$ and $R^6$ have the meanings indicated above, are halogenated in the customary manner (in this context, see J.Org.Chem. 36 (1971) 3,467).

Examples of starting substances of the formula (V) which may be mentioned are:

$$(Br)Cl-CH-\overset{R^5}{\underset{|}{C}}=N-O-R^6 \quad (V)$$
(with $R^4$ substituent shown)

| R⁴ | R⁵ | R⁶ | R⁴ | R⁵ | R⁶ |
|---|---|---|---|---|---|
| H | H | H | H | CH₃ | H |
| H | H | CH₃ | H | CH₃ | CH₃ |
| H | H | C₂H₅ | H | CH₃ | C₂H₅ |
| H | H | n-C₃H₇ | H | CH₃ | n-C₃H₇ |
| H | H | i-C₃H₇ | H | CH₃ | i-C₃H₇ |

-continued $$\underset{(Br)Cl-CH-C=N-O-R^6}{\overset{R^4\phantom{xx}R^5}{|\phantom{xx}|}} \quad (V)$$

| R⁴ | R⁵ | R⁶ | R⁴ | R⁵ | R⁶ |
|---|---|---|---|---|---|
| H | H | n-C₄H₉ | H | CH₃ | n-C₄H₉ |
| H | H | tert.-C₄H₉ | H | CH₃ | tert.-C₄H₉ |
| H | H | —CH₂—CH=CH₂ | H | CH₃ | —CH₂—CH=CH₂ |
| H | H | —CH₂—C≡CH | H | CH₃ | —CH₂—C≡CH |
| H | H | —CH₂—O—CH₃ | H | CH₃ | —CH₂—O—CH₃ |
| H | H | —CH₂—S—CH₃ | H | CH₃ | —CH₂—S—CH₃ |
| H | H | —CH₂—⟨C₆H₅⟩ | H | CH₃ | —CH₂—⟨C₆H₅⟩ |
| H | H | —CH₂—⟨C₆H₄⟩—Cl | H | CH₃ | —CH₂—⟨C₆H₄⟩—Cl |
| H | C₂H₅ | H | CH₃ | H | H |
| H | C₂H₅ | CH₃ | CH₃ | H | CH₃ |
| H | C₂H₅ | C₂H₅ | CH₃ | H | C₂H₅ |
| H | C₂H₅ | n-C₃H₇ | CH₃ | H | n-C₃H₇ |
| H | C₂H₅ | i-C₃H₇ | CH₃ | H | i-C₃H₇ |
| H | C₂H₅ | n-C₄H₉ | CH₃ | H | n-C₄H₉ |
| H | C₂H₅ | tert.-C₄H₉ | CH₃ | H | tert.-C₄H₉ |
| H | C₂H₅ | —CH₂—CH=CH₂ | CH₃ | H | —CH₂—CH=CH₂ |
| H | C₂H₅ | —CH₂—C≡CH | CH₃ | H | —CH₂—C≡CH |
| H | C₂H₅ | —CH₂—O—CH₃ | CH₃ | H | —CH₂—O—CH₃ |
| H | C₂H₅ | —CH₂—S—CH₃ | CH₃ | H | —CH₂—S—CH₃ |
| H | C₂H₅ | —CH₂—⟨C₆H₅⟩ | CH₃ | H | —CH₂—⟨C₆H₅⟩ |
| H | C₂H₅ | —CH₂—⟨C₆H₄⟩—Cl | CH₃ | H | —CH₂—⟨C₆H₄⟩—Cl |
| CH₃ | CH₃ | H | C₂H₅ | H | H |
| CH₃ | CH₃ | CH₃ | C₂H₅ | H | CH₃ |
| CH₃ | CH₃ | C₂H₅ | C₂H₅ | H | C₂H₅ |
| CH₃ | CH₃ | n-C₃H₇ | C₂H₅ | H | n-C₃H₇ |
| CH₃ | CH₃ | i-C₃H₇ | C₂H₅ | H | i-C₃H₇ |
| CH₃ | CH₃ | n-C₄H₉ | C₂H₅ | H | n-C₄H₉ |
| CH₃ | CH₃ | tert.-C₄H₉ | C₂H₅ | H | tert.-C₄H₉ |
| CH₃ | CH₃ | —CH₂—CH=CH₂ | C₂H₅ | H | —CH₂—CH=CH₂ |
| CH₃ | CH₃ | —CH₂—C≡CH | C₂H₅ | H | —CH₂—C≡CH |
| CH₃ | CH₃ | —CH₂—O—CH₃ | C₂H₅ | H | —CH₂—O—CH₃ |
| CH₃ | CH₃ | —CH₂—S—CH₃ | C₂H₅ | H | —CH₂—S—CH₃ |
| CH₃ | CH₃ | —CH₂—⟨C₆H₅⟩ | C₂H₅ | H | —CH₂—⟨C₆H₅⟩ |
| CH₃ | CH₃ | —CH₂—⟨C₆H₄⟩—Cl | C₂H₅ | H | —CH₂—⟨C₆H₄⟩—Cl |
| C₂H₅ | CH₃ | H | | | |
| C₂H₅ | CH₃ | CH₃ | | | |
| C₂H₅ | CH₃ | C₂H₅ | | | |
| C₂H₅ | CH₃ | n-C₃H₇ | | | |
| C₂H₅ | CH₃ | i-C₃H₇ | | | |
| C₂H₅ | CH₃ | n-C₄H₉ | | | |
| C₂H₅ | CH₃ | tert.-C₄H₉ | | | |
| C₂H₅ | CH₃ | —CH₂—CH=CH₂ | | | |
| C₂H₅ | CH₃ | —CH₂—C≡CH | | | |
| C₂H₅ | CH₃ | —CH₂—O—CH₃ | | | |
| C₂H₅ | CH₃ | —CH₂—S—CH₃ | | | |
| C₂H₅ | CH₃ | —CH₂—⟨C₆H₅⟩ | | | |
| C₂H₅ | CH₃ | —CH₂—⟨C₆H₄⟩—Cl | | | |

The formula (VI) provides a general definition of the N-substituted anilides required as starting substances in carrying out process variant (c). In this formula, R¹, R², R³, R⁴, R⁵ and R⁷ preferably have those meanings which have already been mentioned as preferred in connection with the description of the substances of the formula (I).

The N-substituted anilides of the formula (VI) have not hitherto been disclosed in the literature. However, they can be prepared in a simple manner by several processes, for example:

(a) by reacting anilides of the general formula

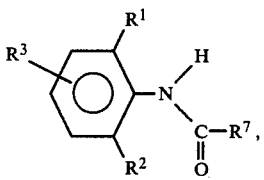

in which
R$^1$, R$^2$, R$^3$ and R$^7$ have the meanings indicated above,
with keto derivatives of the general formula

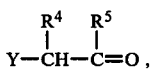

in which
R$^4$, R$^5$ and Y have the meanings indicated above,
in the presence of an acid-binding agent and in the presence of a diluent, or (β) by reacting anilides of the general formula

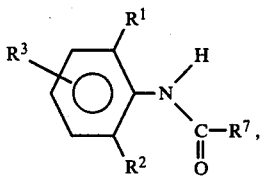

in which
R$^1$, R$^2$, R$^3$ and R$^7$ have the meanings indicated above,
with propargyl halides of the general formula

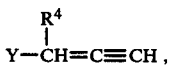

in which
R$^4$ and Y have the meanings indicated above,
in the presence of an acid-binding agent and if appropriate in the presence of a diluent, and hydrating the propargylacetanilides formed, of the general formula

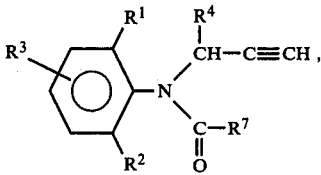

in which
R$^1$, R$^2$, R$^3$, R$^4$ and R$^7$ have the meanings indicated above,
in the customary manner, or (γ) by reacting aniline derivatives of the general formula

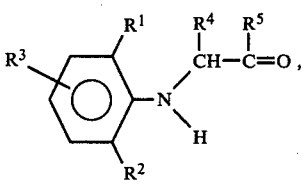

in which
R$^1$, R$^2$, R$^3$, R$^4$ and R$^5$ have the meanings indicated above,
with known acid chlorides or bromides of the general formula

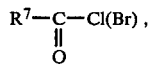

in which
R$^7$ has the meaning indicated above,
in the presence of a diluent and if appropriate in the presence of an acid-binding agent.

Any of the customary acid acceptors can be used as the acid-binding agents in the preparation of the N-substituted acetanilides of the formula (VI) by processes (α), (β) and (γ). An alkali metal carbonate, such as potassium carbonate or sodium carbonate, is preferably used.

Diluents which can be employed in processes (α), (β) and (γ) are any of the customary inert organic solvents. An aromatic solvent, especially toluene, or dimethylformamide is preferably used.

According to a preferred embodiment, the reaction in processes (α) and (β) is carried out in a two-phase system, for example aqueous sodium hydroxide solution or potassium hydroxide solution/toluene or methylene chloride, if appropriate with the addition of 0.1–1 mol of a phase-transfer catalyst, for example an ammonium or phosphonium compound.

The reaction temperatures can be varied within a substantial range in processes (α), (β) and (γ). In general, the reaction is carried out between 0° C. and 180° C., preferably between 20° C. and 160° C.

Equimolar amounts of the reactants are preferably used in the procedure according to processes (α), (β) and (γ). Working up and isolation of the reaction products are effected by customary methods.

In some cases it proves advantageous to prepare the N-substituted acetanilides of the formula (VI) by acid hydrolysis of the compounds of the formula (I).

The formula (VII) provides a general definition of the hydroxylamine (derivatives) also to be used as starting substances for process variant (c). In this formula, R$^6$ preferably has those meanings which have already been mentioned as preferred in connection with the description of the substances of the formula (I). The compounds of the formula (VII) are preferably employed in the form of their hydrohalides, especially as the hydrochlorides.

The formula (IX) provides a general definition of the compounds required as starting substances, in addition to the oximes of the formula (VIII) which are according to the invention, in carrying out process variant (d). In formula (IX), R$^9$ preferably represents straight-chain or branched alkyl with 1 to 4 carbon atoms, alkenyl or alkynyl with in either case 2 to 4 carbon atoms, alkoxyalkyl or alkylthioalkyl with in either case 1 to 4 carbon atoms in the alkyl part and 1 to 4 carbon atoms in the alkoxy or alkylthio part, or optionally substituted aralkyl with 6 to 10 carbon atoms in the aryl part and 1 to 2 carbon atoms in the alkyl part, benzyl being mentioned as preferred, and preferred substituents being the substituents of aryl which have already been mentioned as preferred in the case of R$^6$.

The hydroxylamine (derivatives) of the formula (VII) and the compounds of the formula (IX) are generally known compounds of organic chemistry.

The formula (X) provides a general definition of the halogenoacetanilides required as starting substances in carrying out process variant (e). In this formula, $R^1$, $R^2$, $R^3$, $R^4$, $R^5$ and $R^6$ preferably have those meanings which have already been mentioned as preferred for these substituents in connection with the description of the substances of the formula (I).

The halogenacetanilides of the formula (X) have not hitherto been disclosed in the literature. However, they are the subject of U.S. Ser. No. 086,111 filed Oct. 18, 1979, now abandoned. They can be obtained by the processes indicated in this earlier Application, for example by reacting anilinoalkyl oxime ethers of the formula (II) with halogenoacetic acid chlorides, bromides or anhydrides, analogously to process variant (a); or by reacting halogenoacetanilides with substituted oxime ethers of the formula (V), analogously to process variant (b).

The formula (XI) provides a general definition of the compounds also to be used as starting substances for process variant (e). In this formula, Az and $R^8$ preferably have those meanings which have already been mentioned as preferred in connection with the description of the substances of the formula (I). B preferably represents hydrogen, sodium or potassium.

The compounds of the formula (XI) are generally known compounds of organic chemistry.

The formula (XII) provides a general definition of the hydroxyacetanilides required as starting substances in carrying out process variant (f). In this formula, $R^1$, $R^2$, $R^3$, $R^4$, $R^5$ and $R^6$ preferably have those meanings which have already been mentioned as preferred in connection with the description of the substances of the formula (I).

The hydroxyacetanilides of the formula (XII) can be obtained in a generally known manner, by saponifying acyloxyacetanilides of the general formula

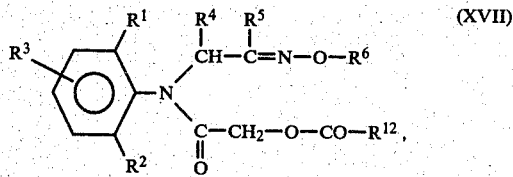

(XVII)

in which $R^1$, $R^2$, $R^3$, $R^4$, $R^5$ and $R^6$ have the meanings indicated above and $R^{12}$ represents alkyl with 1 to 4 carbon atoms, with sodium hydroxide solution or potassium hydroxide solution or with an alkali metal alcoholate of a lower alcohol, for example sodium methylate or sodium ethylate, at temperatures between 20° to 40° C. and, after acidifying the mixture in the customary manner, isolating the compounds of the formula (XII).

The acyloxyacetanilides of the formula (XVII) can be obtained in a generally customary and known manner, for example by replacing the reactive substituent Hal in halogenoacetanilides of the formula (X) by reaction with a lower alkanecarboxylic acid, the acid preferably being employed in the form of an alkali metal salt or alkaline earth metal salt thereof, or by reacting anilinoalkyl oxime ethers of the formula (II) with corresponding acyloxyacetyl halides.

The formula (XIII) provides a general definition of the halides also to be used as starting substances for process variant (f)(1). In this formula, $R^8$ preferably has those meanings which have already been mentioned as preferred in connection with the description of the substances of the formula (I). Hal preferably represents chlorine, bromine or iodine.

The halides of the formula (XIII) are generally known compounds of organic chemistry.

The dihydropyran also to be used as a starting substance for process variant (f)(2) is likewise a known compound of organic chemistry.

Preferred diluents for the reaction, in process variant (a) are inert organic solvents. These include, as preferences, ketones, such as diethyl ketone, and in particular acetone and methyl ethyl ketone; nitriles, such as propionitrile, and in particular acetonitrile; ethers, such as tetrahydrofuran or dioxan; aliphatic and aromatic hydrocarbons, such as petroleum ether, benzene, toluene or xylene; halogenated hydrocarbons, such as methylene chloride, carbon tetrachloride, chloroform or chlorobenzene; and esters, such as ethyl acetate.

If appropriate, process variant (a) can be carried out in the presence of an acid-binding agent (hydrogen halide acceptor). Any of the customary acid-binding agents can be used here. These include, as preferences, organic bases, such as tertiary amines, for example triethylamine, or pyridine, and furthermore inorganic bases, for example alkali metal hydroxides and alkali metal carbonates.

The reaction temperatures can be varied within a substantial range in carrying out process variant (a). In general, the reaction is carried out between 0° C. and 120° C., preferably between 20° and 100° C.

In carrying out process variant (a), 1 to 1.5 mols of acylating agent and 1 to 1.5 mols of acid-binding agent are preferably employed per mol of the compound of the formula (II). Isolation of the resultant compound of the formula (I) is effected in the customary manner.

Preferred diluents for the reaction in process variant (b) are inert organic solvents. These include, as preferences, the solvents already mentioned in the case of process variant (a).

Preferred acid-binding agents in process variant (b) are the substances already mentioned in the case of process variant (a).

The reaction temperatures can be varied within a substantial range in carrying out process variant (b). In general, the reaction is carried out between 0° C. and 150° C., preferably between 20° C. and 100° C.

Equimolar amounts of the reactants are preferably used for carrying out process variant (b). However, it is also possible to employ one of the components in excess. Working up and isolation of the reaction product are effected by customary methods.

In a preferred embodiment, the reaction in process variant (b) is carried out in a two-phase system, for example aqueous sodium hydroxide solution or potassium hydroxide solution/toluene or methylene chloride, if appropriate with the addition of 0.1–1 mol of a phase-transfer catalyst, for example an ammonium or phosphonium compound, examples which may be mentioned being benzyldodecyl-dimethyl-ammonium chloride and triethyl-benzyl-ammonium chloride.

Preferred diluents for the reaction in process variant (c) are alcohols or aqueous alcohols.

If the compounds of the formula (VII) are employed in the form of their salts, preferably as the hydrochlorides, in carrying out process variant (c), the process is carried out in the presence of an acid-binding agent. Preferred acid-binding agents include alkali metal carbonates and acetates.

The reaction temperatures can be varied within a substantial range in carrying out process variant (c). In general, the reaction is carried out between 20° and 120° C., preferably between 40° and 100° C.

Equimolar amounts of the reactants are preferably used in carrying out process variant (c). However, it is also possible to employ one of the components in excess. Working up and isolation of the reaction product are effected by customary methods.

Possible diluents for the reaction in process variant (d) are any of the inert organic solvents. These include, as preferences, ethers, such as diethyl ether or dioxan; aromatic hydrocarbons, such as toluene or benzene; in some cases also chlorinated hydrocarbons, such as chloroform, methylene chloride or carbon tetrachloride; and hexamethylphosphoric acid triamide or dimethylformamide.

The reaction temperatures can be varied within a substantial range in carrying out process variant (d). In general, the reaction is carried out between 20° and 150° C., preferably at room temperature. In some cases it is advantageous to carry out the reaction at the boiling point of the solvent, for example between 60° and 100° C.

In carrying out process variant (d), 1 to 3 mols of the compound of the formula (IX) are preferably employed per mol of alkali metal salt of an oxime of the formula (VIII). Working up and isolation of the reaction product are effected by customary methods.

In a preferred embodiment of process variant (d), the appropriate procedure followed is to use an oxime of the formula (VIII) as the starting material, to convert the oxime into a salt, in a suitable inert organic solvent, by means of an alkali metal hydride or amide, and to react the salt immediately, without isolation, with a halide of the formula (IX), the compound of the formula (I) being obtained in one operation with elimination of an alkali metal halide.

According to another preferred embodiment of process (d), the preparation of the salts of the oximes of the formula (VIII) and the reaction according to the invention are appropriately carried out in a two-phase system, for example aqueous sodium hydroxide solution or potassium hydroxide solution/toluene or methylene chloride, with the addition of 0.1–1 mol of a phase-transfer catalyst, for example an ammonium or phosphonium compound.

Preferred diluents for the reaction in process variant (e) are inert organic solvents. These include, as preferences, the solvents already mentioned in the case of process variant (a).

If appropriate, the reaction according to process variant (e) can be carried out in the presence of an acid-binding agent. It is possible to add any of the inorganic or organic acid-binding agents which can customarily be used, such as alkali metal carbonates, for example sodium carbonate, potassium carbonate and sodium bicarbonate, or such as lower tertiary alkylamines, cycloalkylamines or aralkylamines, for example triethylamine or dimethylbenzylamine; or such as pyridine and diazabicyclooctane. An excess of azole is preferably used.

The reaction temperatures can be varied within a substantial range in process variant (e). In general, the reaction is carried out between 20° and 150° C., preferably at from 60° to 120° C. If a solvent is present, the reaction is appropriately carried out at the boiling point of the particular solvent. In carrying out process variant (e), 1 to 2 mols of the compound of the formula (XI) and, if appropriate, 1 to 2 mols of acid-binding agent are preferably employed per mol of the compound of the formula (X). Isolation of the resultant compound of the formula (I) is effected in the customary manner.

Preferred diluents for the reaction in process variant (f) are inert organic solvents. These include, as preferences, the solvents already mentioned in the case of process variant (a).

If appropriate, the reaction according to process variant (f) (1) can be carried out in the presence of an acid-binding agent. It is possible to add any of the inorganic or organic acid-binding agents which can customarily be used. These include, as preferences, the compounds already mentioned in the case of process variant (a).

The reaction temperatures can be varied within a substantial range in process variant (f) (1). In general, the reaction is carried out between 20° and 150° C., preferably at the boiling point of the solvent, for example between 60° and 100° C.

In carrying out process variant (f) (1), 1 mol of halide of the formula (XIII) and, if appropriate, 1 to 2 mols of acid-binding agent are generally employed per mol of the compound of the formula (XII), if appropriate after adding 1 to 2 mols of a strong base, for example an alkali metal hydride. To isolate the end product, the reaction mixture is freed from the solvent, and water and an organic solvent are added to the residue. The organic phase is separated off and worked up in the customary manner.

According to a preferred embodiment of process (f) (1), the appropriate procedure is to use a hydroxyacetanilide of the formula (XII) as the starting material, to convert this hydroxyacetanilide into an alkali metal alkanolate, in a suitable inert solvent, by means of an alkali metal hydride or bromide, and to react the alkanolate immediately, without isolation, with a halide of the formula (XIII), the compound of the formula (I) being obtained in one operation with elimination of an alkali metal halide.

If appropriate, the reaction according to process variant (f) (2) can be carried out in the presence of a catalyst. Hydrogen chloride is preferably used for this (see J. Am. Chem. Soc. 69, 2,246 (1947), ibid. 70, 4,187 (1948).

The reaction temperatures can be varied within a substantial range in process variant (f) (2). In general, the reaction is carried out between 0° and 100° C., preferably between 20° and 60° C.

Equimolar amounts of the reactants are preferably used in carrying out process variant (f) (2). Isolation of the resultant compound of the formula (I) is effected in the customary manner.

The active compounds according to the invention exhibit a powerful microbicidal action and can be employed in practice for combating undesired microorganisms. The active compounds are suitable for use as plant protection agents.

Fungicidal agents in plant protection are employed for combating Plasmodiophoromycetes, Oomycetes, Chytridiomycetes, Zygomycetes, Ascomycetes, Basidiomycetes and Deuteromycetes.

The good toleration, by plants, of the active compounds, at the concentrations required for combating plant diseases, permits treatment of above-ground parts of plants, of vegetative propagation stock and seeds, and of the soil.

As plant protection agents, the active compounds according to the invention can be used with particularly good success for combating Oomycetes, for example the blight and brown rot of tomato and potato causative organism (*Phytophthora infestans*), and *Pyricularia oryzae* in rice. It should be particularly emphasised that the active compounds according to the invention display not only a protective action but also a curative/eradicative action. They also have systemic properties. Thus, it is possible to protect plants from fungal attack if the active compound is fed to the above-ground parts of the plant via the soil and the roots or via the seed.

The active compounds can be converted into the customary formulations. Such as solutions, emulsions, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention can be present in the formulations, or in the various use forms, as a mixture with other active compounds, such as fungicides, bactericides, insecticides, acaricides, nematicides, herbicides, bird repellents growth factors, plant nutrients and agents for improving soil structure.

The active compounds can be used as such, as their formulations or as the use forms prepared therefrom by further dilution, such as ready-to-use solutions, emulsions, suspensions, powders, pastes and granules. They may be used in the customary manner, for example by watering, immersion, spraying, atomizing, misting, vaporizing, injecting, brushing on, dusting, scattering, dry dressing, moist dressing, wet dressing, slurry dressing or encrusting.

In the treatment of parts of plants, the active compound concentrations in the use forms can be varied within a substantial range. They are, in general, from 1 to 0.0001% by weight, preferably from 0.5 to 0.001%.

In the treatment of seed, amounts of active compound of, in general, 0.001 to 50 g, preferably 0.01 to 10 g, are employed per kilogram of seed.

For the treatment of soil, active compound concentrations of, in general, 0.00001 to 0.1% by weight, preferably 0.0001 to 0.02%, are employed at the place of action.

The present invention also provides a fungicidal composition containing as active ingredient a compound of the present invention in admixture with a solid or liquefied gaseous diluent or carrier or in admixture with a liquid diluent or carrier containing a surface-active agent.

The present invention also provides a method of combating fungi which comprises applying to the fungi, or to a habitat thereof, a compound of the present invention alone or in the form of a composition containing as active ingredient a compound of the present invention in admixture with a diluent or carrier.

The present invention further provides crops protected from damage by fungi by being grown in areas in which immediately prior to and/or during the time of the growing a compound of the present invention was applied alone or in admixture with a diluent or carrier.

It will be seen that the usual methods of providing a harvested crop may be improved by the present invention.

PREPARATIVE EXAMPLES

EXAMPLE 1

(a) 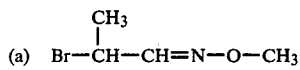

51.9 g (0.6 mol) of 1-methoxyimino-propane and 106.7 g (0.6 mol) of N-bromo-succinimide in 400 ml of carbon tetrachloride were heated to the boiling point, and heated under reflux for 2.5 hours, while irradiating. After cooling the mixture and filtering off the succinimide, the filtrate was distilled, first under normal pressure and then under a waterpump vacuum. 68 g (68% of theory) of 2-bromo-1-methoxyimino-propane of boiling point 49°–50° C./20 mm Hg and with a refractive index of $n_D^{20} = 1.4750$ were obtained.

(b) 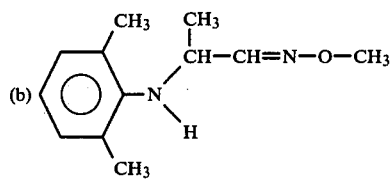

42.4 g (0.35 mol) of 2,6-dimethylaniline and 25 g (0.17 mol) of powdered potassium carbonate in 100 ml of dimethylformamide were heated to 80° C., whilst stirring, and 29 g (0.17 mol) of 2-bromo-1-methoxyiminopropane were added dropwise. During this addition, the temperature rose to 95° C. The mixture was stirred for a further 2 hours at 80° C., the inorganic salt was filtered off and the filtrate was distilled. After distilling off the solvent and the excess 2,6-dimethylaniline, 25.4 g (72.5% of theory) of N-(1-methoxyimino-prop-2-yl)-2,6-dimethylaniline of boiling point 107°–109° C./0.1 mm Hg were obtained.

(c) 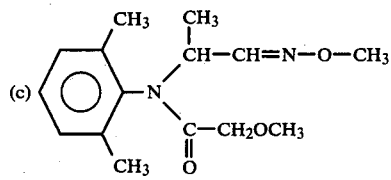 (1)

Process variant (a)

10.3 g (0.05 mol) of N-(1-methoxyimino-prop-2-yl)-2,6-dimethyl-aniline and 5 g (0.063 mol) of anhydrous pyridine were dissolved in 100 ml of anhydrous tetrahydrofuran, and 6.89 (0.063 mol) of methoxyacetic acid chloride were added at 60° C., while stirring. The mixture was heated for a further hour under reflux and the solvent was then distilled off in vacuo and the residue was taken up on water/methylene chloride. The organic phase was separated off, dried over sodium sulphate and concentrated. The oily residue was distilled in vacuo in a bulb tube apparatus, 11.5 g (83% of theory) of 2,6-dimethyl-N-(1-methoxyimino-prop-2-yl)-N-methoxyacetylaniline of boiling point 140° C./0.2 mm Hg and with a refractive index of $n_D^{20} = 1.5261$ were obtained.

EXAMPLE 2

(a) 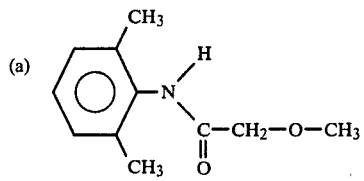

55 g (0.5 mol) of methoxyacetyl chloride were added dropwise to a solution of 61 g (0.5 mol) of 2,6-dimethylaniline and 50.5 g (0.5 mol) of triethylamine in 250 ml of toluene at 5° to 15° C., while stirring and cooling. The mixture was subsequently stirred at 20° C. for 2 hours, filtered and concentrated and the residue was taken up in water. The aqueous mixture was extracted with methylene chloride and the extract was dried over sodium sulphate and concentrated by distilling off the solvent. The residue was distilled under a high vacuum. 55 g (57% of theory) of 2,6-dimethyl-N-methoxyacetyl-aniline of boiling point 122°–132° C./0.1 mm Hg and of melting point 61°–63° C. were obtained.

(b) 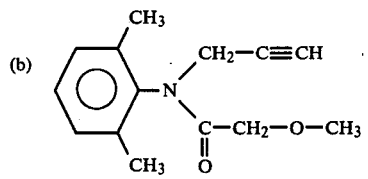

30 g (0.155 mol) of 2,6-dimethyl-N-methoxyacetylaniline and 0.3 g of triethyl-benzyl-ammonium chloride were dissolved in a two-phase system mixture of 100 ml of 50% strength sodium hydroxide solution and 250 ml of toluene, and 19 g (0.016 mol) of propargyl bromide were added, whilst stirring vigorously. The mixture was stirred for 4 hours and the toluene phase was separated off, washed several times with water, dried over sodium sulphate and concentrated by distilling off the solvent under a waterpump vacuum. The residue was distilled under a high vacuum. 26.5 g (74% of theory) of 2,6-dimethyl-N-methoxyacetyl-N-propargyl-aniline of boiling point 140°/0.4 mm Hg and of melting point 49°–51° C. were obtained.

(c) 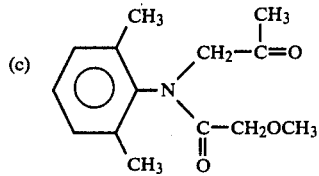

23.1 g (0.1 mol) of 2,6-dimethyl-N-methoxyacetyl-N-propargyl-aniline in 150 ml of 85% strength formic acid were heated to 80° C., and 0.5 g of mercury sulphate was then added to the reaction mixture. The mixture was stirred for a further 6 hours at 80° C. and, after cooling, saturated ammonium sulphate solution was added to the solution and the mixture was extracted with methylene chloride. After naturalizing the methylene chloride phase with sodium bicarbonate solution, the organic phase was dried with sodium sulphate and concentrated. 20.5 g (77% of theory) of 2,6-dimethyl-N- acetonyl-N-methoxyacetyl-aniline of melting point 56°–57° C. were obtained.

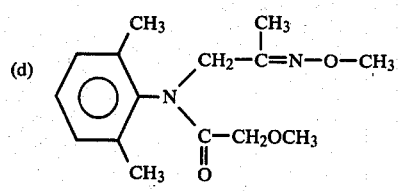  (2)

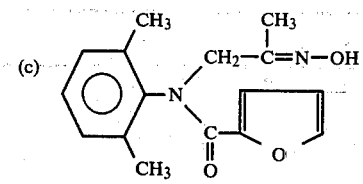  (3)

Process variant (c)

20 g (0.08 mol) of 2,6-dimethyl-N-methoxyacetyl-N-acetonylaniline, 7.5 g (0.09 mol) of O-methyl-hydroxylamine hydrochloride and 9.1 g (0.09 mol) of triethylamine in 100 ml of ethanol were heated under reflux for 5 hours. After distilling off the solvent in vacuo, the residue was partitioned between water/methylene chloride. The organic phase was separated off, dried over sodium sulphate and concentrated. After adding petroleum ether, the residue crystallized. 21 g (94% of theory) of 2,6-dimethyl-N-(2-methoxyimino-prop-1-yl)-N-methoxyacetylaniline of melting point 56°–57° C. were obtained.

EXAMPLE 3

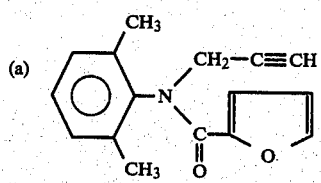  (a)

15.9 g (0.1 mol) of 2,6-dimethyl-N-propargyl-aniline and 8 g (0.1 mol) of pyridine in 100 ml of tetrahydrofuran were heated to the boiling point, and 13 g (0.1 mol) of furane-2-carboxylic acid chloride were carefully added. The reaction mixture was stirred under reflux for 15 minutes and then concentrated by distilling off the solvent in vacuo. The residue was taken up in methylene chloride and washed with water.

The organic phase was separated off, dried over sodium sulphate and concentrated. The residue crystallized after trituration with petroleum ether. 22.5 g (89% of theory) of 2,6-dimethyl-N-(2-furoyl)-N-propargyl-aniline of melting point 109°–112° C. were obtained.

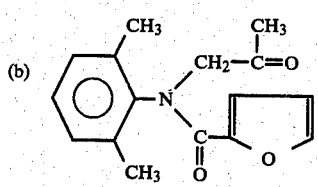  (b)

This compound was obtained analogously to Example 2, by reaction of 2,6-dimethyl-N-(2-furoyl)-N-propargyl-aniline. 2,6-Dimethyl-N-acetonyl-N-(2-furoyl)-aniline of melting point 90°–91° C. was obtained in 84% yield.

Process variant (c)

27.1 g (0.1 mol) of 2,6-dimethyl-N-acetonyl-N-(2-furoyl)-aniline, 14 g (0.2 mol) of hydroxyammonium chloride and 15 ml of triethylamine in 150 ml of ethanol were heated under reflux for 3 hours. The reaction mixture was then largely freed from solvent in vacuo, the residue was taken up in methylene chloride and the methylene chloride mixture was washed with water, dried over sodium sulphate and concentrated. The crystalline residue was triturated with ether and the solid was filtered off. 24.4 g (85% of theory) of 2,6-dimethyl-N-(2-furoyl)-N-(2-hydroxyimino-prop-1-yl)-aniline of melting point 155°–156° C. were obtained.

EXAMPLE 4

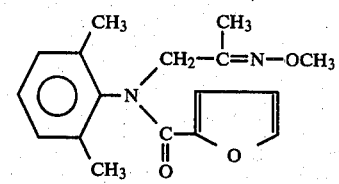

Process variant (d)

7 g (0.024 mol) of 2,6-dimethyl-N-(2-furoyl)-N-(2-hydroxyimino-prop-1-yl)-aniline (Example 3) and 0.5 g of triethylbenzylammonium chloride were dissolved in a two-phase mixture of 30 ml of 50% strength sodium hydroxide solution and 100 ml of methylene chloride, and 3.7 g (0.03 mol) of dimethyl sulphate were added, while stirring vigorously. During this addition, the temperature rose from about 20° C. to about 32° C. After stirring the mixture at room temperature for 12 hours, the phases were separated. The organic phase was washed again with water, dried over sodium sulphate and concentrated. The resulting dark oil was distilled in a bulb tube apparatus (boiling point 170° C./0.1 mm Hg). The product (2.3 g) which had crystallized out was recrystallized from petroleum ether. 1.4 g (20% of theory) of 2,6-dimethyl-N-(2-furoyl)-N-(2-methoxyimino-prop-1-yl)-aniline of melting point 108°–109° C. were obtained.

The following compounds of the general formula

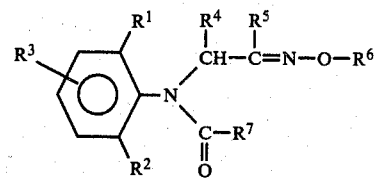  (I)

were obtained analogously to Examples 1 to 4 and according to process variants (a) to (f):

| Compound No. | $R^1$ | $R^2$ | $R^3$ | $R^4$ | $R^5$ | $R^6$ | $R^7$ | Physical constants |
|---|---|---|---|---|---|---|---|---|
| 5 | $CH_3$ | $CH_3$ | H | H | $CH_3$ | H | $-CH_2OCH_3$ | Melting point :120–23° C. |
| 6 | $CH_3$ | $CH_3$ | H | H | H | $CH_3$ | $-CH_2OCH_3$ | $n_D^{20}$:1.5261 |
| 7 | $CH_3$ | $CH_3$ | H | H | H | $CH_3$ |  | Melting point :85–91° C. |
| 8 | $CH_3$ | $CH_3$ | H | $CH_3$ | $CH_3$ | $CH_3$ | $-CH_2OCH_3$ | $n_D^{20}$:1.5235 |
| 9 | $CH_3$ | $CH_3$ | H | $CH_3$ | H | $CH_3$ |  | $n_D^{20}$:1.5602 |
| 10 | $CH_3$ | $CH_3$ | H | $CH_3$ | $CH_3$ | $CH_3$ |  | $n_D^{20}$:1.5600 |
| 11 | $CH_2$ | $C_2H_5$ | H | H | H | $C_2H_5$ | $-CH_2OCH_3$ | $n_D^{20}$:1.5212 |
| 12 | $CH_3$ | $CH_3$ | H | $CH_3$ | $CH_3$ | $CH_3$ | $-CHCl_2$ | Melting point :66–68° C. |
| 13 | $CH_3$ | $CH_3$ | H | H | H | $C_2H_5$ | $-CH_2OCH_3$ | $n_D^{20}$:1.5210 |
| 14 | $CH_3$ | $CH_3$ | H | H | H | $C_3H_7$ | $-CH_2OCH_3$ | $n_D^{20}$:1.5173 |
| 15 | $CH_3$ | $CH_3$ | H | $CH_3$ | H | $C_2H_5$ | $-CHCl_2$ | $n_D^{20}$:1.5355 |
| 16 | $CH_3$ | $CH_3$ | H | $CH_3$ | H | $C_2H_5$ | $-CH_2OCH_3$ | $n_D^{20}$:1.5182 |
| 17 | $CH_3$ | $CH_3$ | H | $CH_3$ | H | $CH_3$ | $-COOCH_3$ | $n_D^{20}$:1.5188 |
| 18 | $CH_3$ | $CH_3$ | H | $CH_3$ | H | $CH_3$ | $-CHCl_2$ | $n_D^{20}$:1.5427 |
| 19 | $CH_3$ | $CH_3$ | H | $CH_3$ | H | $CH_3$ |  | $n_D^{20}$:1.5334 |
| 20 | $CH_3$ | $CH_3$ | H | $CH_3$ | H | $CH_3$ | 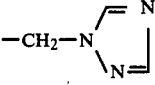 | Melting point :81–104° C. |
| 21 | $CH_3$ | $C_2H_5$ | H | $CH_3$ | H | $CH_3$ | $-CH_2OCH_3$ | $n_D^{20}$:1.5231 |
| 22 | $CH_3$ | $C_2H_5$ | H | $CH_3$ | H | $C_2H_5$ | $-CH_2OCH_3$ | $n_D^{20}$:1.5180 |
| 23 | $C_2H_5$ | $C_2H_5$ | H | $CH_3$ | H | $C_2H_5$ | $-CH_2OCH_3$ | $n_D^{20}$:1.5172 |
| 24 | $CH_3$ | $CH_3$ | H | H | H | $CH_3$ | $-CHCl_2$ | Melting point :73–78° C. |
| 25 | $CH_3$ | $CH_3$ | H | H | $CH_3$ | $-CH_2-CH=CH_2$ | $-CH_2OCH_3$ | Bp. 150° C. 0.1mm |
| 26 | $CH_3$ | $CH_3$ | H | H | $CH_3$ | 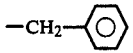 | $-CH_2OCH_3$ | Mp. 60–62° C. |
| 27 | $CH_3$ | $CH_3$ | H | H | H | $CH_3$ | 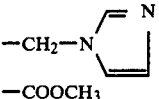 | oil |
| 28 | $CH_3$ | $CH_3$ | H | H | H | $CH_3$ | $-COOCH_3$ | Bp. 170° C. 0.2mm |
| 29 | Cl | $CH_3$ | H | $CH_3$ | H | $CH_3$ | $-CH_2OCH_3$ | $n_D^{20}$:1.5323 |
| 30 | $CH_3$ | $CH_3$ | H | H | H | $CH_3$ | 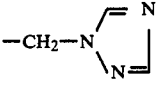 | $n_D^{20}$:1.5528 |
| 31 | $CH_3$ | $CH_3$ | H | $CH_3$ | $CH_3$ | $CH_3$ | $-COOCH_3$ | $n_D^{20}$:1.5195 |
| 32 | $CH_3$ | $CH_3$ | H | $CH_3$ | $CH_3$ | $CH_3$ | 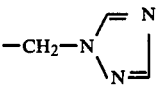 | Mp. 101–08° C. |
| 33 | $CH_3$ | $CH_3$ | H | $C_2H_5$ | H | $CH_3$ | $-CH_2OCH_3$ | $n_D^{20}$:1.5221 |
| 34 | $CH_3$ | $CH_3$ | H | H | H | $CH_3$ | $-CH_2-OCH_2-C\equiv CH$ | Mp. 85–87° C. |
| 35 | $CH_3$ | $CH_3$ | H | H | $CH_3$ | 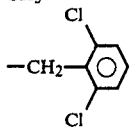 | $-CH_2OCH_3$ | Mp. 72–74° C. |
| 36 | $CH_3$ | $CH_3$ | H | H | H | $CH_3$ | $-CH=CH-CH_3$ | $n_D^{20}$:1.5419 |
| 37 | $CH_3$ | $CH_3$ | H | $CH_3$ | H | $CH_3$ | $-CH=CH-CH_3$ | $n_D^{20}$:1.5371 |
| 38 | $CH_3$ | $CH_3$ | H | H | H | $CH_3$ | $-CH=C(CH_3)_2$ | $n_D^{20}$:1.5381 |
| 39 | $CH_3$ | $CH_3$ | H | $CH_3$ | H | $CH_3$ | $-CH_2-OCH_2-CH=CH_2$ | $n_D^{20}$:1.5238 |
| 40 | $CH_3$ | $CH_3$ | H | $CH_3$ | H | $CH_3$ | $-CH_2OC_2H_5$ | $n_D^{20}$:1.5170 |
| 41 | $CH_3$ | $CH_3$ | H | H | H | $CH_3$ | $-CH_2OC_2H_5$ | $n_D^{20}$:1.5183 |
| 42 | $CH_3$ | $CH_3$ | H | $CH_3$ | H | $CH_3$ | $-CH_2-OCH_2-C\equiv CH$ | oil |
| 43 | $CH_3$ | $CH_3$ | H | H | H | H | $-CH_2OCH_3$ | Fp.:101–08° C. |

The fungicidal activity of the compounds of this invention is illustrated by the following examples wherein the compounds according to the present invention are each identified by the number (given in brackets) for Examples 1 to 4 hereinabove:

The known comparison compound is identified as follows:

(A) = N-Chloroacetyl-N-(2-ethyl-6-methylphenyl)-alanine ethyl ester

[structure: 2-ethyl-6-methylphenyl group with N bearing CH(CH₃)—C(=O)—O—C₂H₅ and C(=O)—CH₂Cl]

EXAMPLE 5

Phytophthora test (tomato)/protective
  Solvent: 4.7 parts by weight of acetone
  Emulsifier: 0.3 part by weight of alkylaryl polyglycol ether
  Water: 95 parts by weight The amount of the active compound required for the desired concentration of the active compound in the spray liquid was mixed with the stated amount of solvent and the concentrate was diluted with the stated amount of water which contained the stated amount of emulsifier.

Young tomato plants with 2 to 4 foliage leaves were sprayed with the spray liquid until dripping wet. The plants remained in a greenhouse for 24 hours at 20 deg.C. and at a relative atmospheric humidity of 70%. The tomato plants were then inoculated with an aqueous spore suspension of *Phytophthora infestans*. The plants were brought into a moist chamber with an atmospheric humidity of 100% and a temperature of 18-20 deg.C.

After 5 days the infection of the tomato plants was determined. The assessment data were converted to percent infection: 0% meant no infection; 100% meant that the plants were totally infected.

In this test, for example, the following compounds showed a very good action which was significantly superior to that of the compound (A) known from the prior art: (5), (3), (6), (8) and (1).

EXAMPLE 6

Phytophthora test (tomato)systemic
  Solvent: 4.7 parts by weight of acetone
  Emulsifier: 0.3 part by weight of alkylaryl polyglycol ether
  Water: 95 parts by weight The amount of active compound required for the desired concentration of the active compound in the watering liquid was mixed with the stated amount of solvent and the concentrate was diluted with the stated amount of water which contained the stated amount of the emulsifier.

Tomato plants grown in standard soil and having 2 to 4 foliage leaves were watered three times in the course of one week with 10 ml of the watering liquid, having the stated concentration of active compound, per 100 ml of soil.

The plants treated in this way were inoculated, after the treatment, with an aqueous spore suspension of *Phytophthora infestans*. The plants were brought into a humidity chamber at an atmospheric humidity of 100% and a temperature of 18 to 20 deg.C. After 5 days, the infection of the tomato plants was determined. The assessment data obtained were converted to percent infection. 0% denoted no infection and 100% denoted that the plants were totally infected.

In this test, for example, the following compounds showed a very good action which was significantly superior to that of the compound (A) known from the prior art: (3), (2), (8) and (1).

It will be appreciated that the instant specification and examples are set forth by way of illustration and not limitation, and that various modifications and changes may be made without departing from the spirit and scope of the present invention.

What is claimed is:

1. An N-oximinoalkyl-anilide of the formula

[structure: phenyl ring with substituents $R^1$, $R^2$, $R^3$, attached to N which bears $CH(R^4)-C(R^5)=N-O-R^6$ and $C(=O)-R^7$]

in which
  $R^1$ represents hydrogen, alkyl of up to 4 carbon atoms or halogen,
  $R^2$ represents alkyl of up to 4 carbon atoms,
  $R^3$ represents hydrogen or alkyl of up to 4 carbon atoms,
  $R^4$ represents hydrogen or alkyl of up to 4 carbon atoms,
  $R^5$ represents hydrogen or alkyl of up to 4 carbon atoms,
  $R^6$ represents hydrogen; alkyl, alkenyl or alkynyl of up to 4 carbon atoms; alkoxyalkyl or alkylthioalkyl of up to 4 carbon atoms in each alkyl moiety; or optionally substituted aralkyl with 6 to 10 carbon atoms in the aryl part and 1 to 2 carbon atoms in the alkyl part wherein the substituents are selected from the group consisting of halogen, straight-chain or branched alkyl of 1 to 4 carbon atoms, halogenoalkyl of 1 to 2 carbon atoms and 1 to 5 halogen atoms, alkoxy of 1 to 2 carbon atoms, alkylthio of 1 to 2 carbon atoms, cyano and nitro, and
  $R^7$ represents furyl, tetrahydrofuryl, thiophenyl, or tetrahydrothiophenyl; isoxazolyl which is optionally substituted by alkyl, alkyl, alkenyl, or alkynyl of up to 4 carbon atoms, in each case optionally substituted by cyano or thiocyano; cycloalkyl of 3 to 7 carbon atoms; or the grouping $-CH_2Az$, $-CH_2-OR^8$, $-CH_2-SR^8$, $-OR^8$, $-SR^8$, $-CH_2-OSO_2R^8$, $-COOR^8$ or

[structure: $-CH_2-O-$ tetrahydropyran-2-yl]

wherein
  $R^8$ represents an alkyl, alkenyl or alkynyl radical of up to 4 carbon atoms optionally substituted by halogen, cyano or thiocyano, or an alkoxyalkyl radical of up to 4 carbon atoms in each alkyl moiety; and
  Az represents pyrazol-1-yl, 1,2,4-triazol-1-yl or imidazol-1-yl.

2. A compound according to claim 1, in which

R[1] represents hydrogen, straight-chain or branched alkyl with 1 to 4 carbon atoms, fluorine, chlorine or bromine, R[6] represents hydrogen, straight-chain or branched alkyl with 1 to 4 carbon atoms, alkenyl or alkynyl with in either case 2 to 4 carbon atoms, alkoxyalkyl or alkylthioalkyl with in either case 1 to 4 carbon atoms in the alkyl part and 1 to 4 carbon atoms in the alkoxy or alkylthio part, or optionally substituted aralkyl with 6 to 10 carbon atoms in the aryl part and 1 to 2 carbon atoms in the alkyl part, each substituent being selected from halogen, straight-chain or branched alkyl with 1 to 4 carbon atoms, halogenoalkyl with 1 to 2 carbon atoms and 1 to 5 halogen atoms, alkoxy with 1 to 2 carbon atoms, alkylthio with 1 to 2 carbon atoms, cyano and nitro, R[7] represents furyl, tetrahydrofuryl, thiophenyl or tetrahydrothiophenyl; isoxazolyl which is optionally substituted by methyl or ethyl; alkyl with 1 to 4 carbon atoms or alkenyl or alkynyl with in either case 2 to 4 carbon atoms, in each case optionally substituted by cyano or thiocyano; cycloalkyl with 3 to 7 carbon atoms; or the grouping —CH$_2$—Az, —CH$_2$—OR[8], —CH$_2$—SR[8], —OR[8], —SR[8], —CH$_2$—OSO$_2$R[8], —COOR[8] or

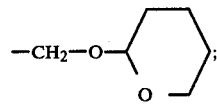

Az represents pyrazol-1-yl, 1,2,4-triazol-1-yl or imidazol-1-yl; and

R[8] represents alkyl with 1 to 4 carbon atoms or alkenyl or alkynyl with in either case 2 to 4 carbon atoms, in each case optionally substituted by halogen, cyano or thiocyano, or represents alkoxyalkyl with 1 to 4 carbon atoms in each alkyl part.

3. A compound according to claim 1, wherein such compound is 2,6-dimethyl-N-(1-methoxyimino-prop-2-yl)-N-methoxyacetyl-aniline of the formula

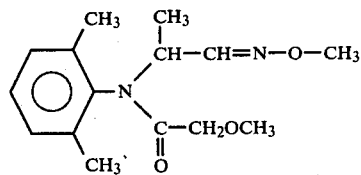

4. A compound according to claim 1, wherein such compound is 2,6-dimethyl-N-(2-furoyl)-N-(2-hydroxyimino-prop-1-yl)-aniline of the formula

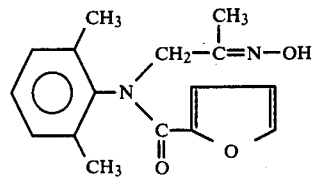

5. A compound according to claim 1, wherein such compound is 2,6-dimethyl-N-(1-methoxyimino-eth-2-yl)-N-methoxyacetylaniline of the formula

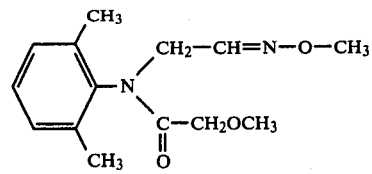

6. A compound according to claim 1, wherein such compound is 2,6-dimethyl-N-(1-ethoxyimino-prop-2-yl)-N-methoxyacetyl-aniline of the formula

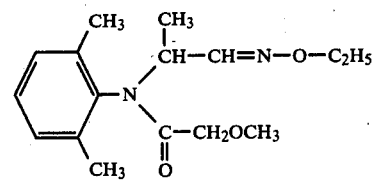

7. A compound according to claim 1, wherein such compound is 2-chloro-6-methyl-N-(1-methoxyimino-prop-2-yl)-N-methoxyacetyl-aniline of the formula

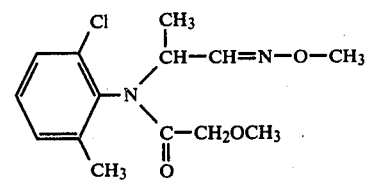

8. A fungicidal composition containing as active ingredient a fungicidally effective amount of a compound according to claim 1 in admixture with a diluent.

9. A method of combating fungi which comprises applying to the fungi, or to a habitat thereof, a fungicidally effective amount of a compound according to claim 1.

10. The method according to claim 9, in which said compound is
2,6-dimethyl-N-(1-methoxyimino-prop-2-yl)-N-methoxyacetyl-aniline,
2,6-dimethyl-N-(2-furoyl)-N-(2-hydroxyimino-prop-1-yl)-aniline,
2,6-dimethyl-N-(1-methoxyimino-eth-2-yl)-N-methoxyacetyl-aniline,
2,6-dimethyl-N-(1-ethoxyimino-prop-2-yl)-N-methoxyacetyl-aniline or
2-chloro-6-methyl-N-(1-methoxyimino-prop-2-yl)-N-methoxyacetyl-aniline.

* * * * *